United States Patent
Leban et al.

(10) Patent No.: US 8,106,048 B2
(45) Date of Patent: *Jan. 31, 2012

(54) HETEROCYCLIC NF-κB INHIBITORS

(75) Inventors: Johann Leban, Planegg (DE); Harald Schmitt, Mainz (DE); Kristina Wolf, Kottgeisering (DE); Stefano Pegoraro, Planegg (DE); Andreas Wuzik, Untermeitingen (DE)

(73) Assignee: 4SC AG, Martinsreid (DE)

( * ) Notice: Subject to any disclaimer, the term of this patent is extended or adjusted under 35 U.S.C. 154(b) by 1007 days.

This patent is subject to a terminal disclaimer.

(21) Appl. No.: 11/575,647

(22) PCT Filed: Jul. 29, 2005

(86) PCT No.: PCT/EP2005/008261
§ 371 (c)(1),
(2), (4) Date: Feb. 29, 2008

(87) PCT Pub. No.: WO2006/032322
PCT Pub. Date: Mar. 30, 2006

(65) Prior Publication Data
US 2008/0261971 A1    Oct. 23, 2008

Related U.S. Application Data

(60) Provisional application No. 60/612,794, filed on Sep. 27, 2004.

(30) Foreign Application Priority Data

Sep. 20, 2004   (EP) ..................................... 04022363

(51) Int. Cl.
*A61K 31/535* (2006.01)
*A61K 31/53* (2006.01)
*A61K 31/497* (2006.01)
*A61K 31/4965* (2006.01)
*A61K 31/445* (2006.01)
*A61K 31/425* (2006.01)
*C07D 403/10* (2006.01)
*C07D 401/10* (2006.01)

(52) U.S. Cl. .................. 514/233.8; 514/242; 514/253.1; 514/254.02; 514/255.05; 514/316; 514/365; 544/133; 544/182; 544/364; 544/405; 546/187

(58) Field of Classification Search ............... 514/233.8, 514/242, 253.1, 254.02, 255.05, 316, 365; 544/133, 182, 364, 405; 546/187
See application file for complete search history.

(56) References Cited

U.S. PATENT DOCUMENTS
2007/0219190 A1* 9/2007 Leban et al. ............. 514/229.8
2008/0261971 A1* 10/2008 Leban et al. ............. 514/233.8
2010/0003258 A1* 1/2010 Weng et al. ............. 424/139.1

FOREIGN PATENT DOCUMENTS

| DE | 102 08 256 | 9/2003 |
|---|---|---|
| EP | 1 352 650 A1 | 10/2003 |
| FR | 1 516 777 | 2/1968 |
| FR | 2 270 848 | 12/1975 |
| WO | 97/15567 | 5/1997 |
| WO | 2004/014882 | 2/2004 |
| WO | 2004/018453 | 3/2004 |
| WO | 2004/041815 | 5/2004 |
| WO | 2004/058751 | 7/2004 |

(Continued)

OTHER PUBLICATIONS

International Search Report (Dated Dec. 1, 2006).

(Continued)

*Primary Examiner* — James O Wilson
*Assistant Examiner* — Ebenezer O Sackey
(74) *Attorney, Agent, or Firm* — Baker Donelson Bearman, Caldwell & Berkowitz, PC

(57) ABSTRACT

The present invention relates to compounds of the general formula (I) and salts and physiologically functional derivatives thereof, (I) wherein $R^1$ is independently hydrogen, alkyl, cycloalkyl, hydroxyalkyl, haloalkyl, haloalkyloxy, aryl, substituted aryl, heteroaryl, substituted heteroaryl, arylalkyl or substituted arylalkyl; $R^2$ is independently —$NR^3R^4$, (II) or (III) $R^3$ is independently alkyl, cycloalkyl, alkoxy, alkylamine, —OH, —SH, alkylthio, hydroxyalkyl, haloalkyl, haloalkyloxy, aryl or heteroaryl, $R^4$ is independently alkyl, cycloalkyl, alkoxy, alkylamine, alkylthio, hydroxyalkyl, haloalkyl, haloalkyloxy, aryl or heteroaryl; $R^5$ is independently H, $COR^6$, $CO_2R^6$, $SOR^6$, $SO_2R^6$, $SO_3R^6$, alkyl, cycloalkyl, alkoxy, —$NH_2$, alkylamine, —$NR^7COR^6$, halogen, —OH, —SH, alkylthio, hydroxyalkyl, haloalkyl, haloalkyloxy, aryl or heteroaryl; $R^6$ is independently H, alkyl, cycloalkyl, —$NH_2$, alkylamine, aryl or heteroaryl; $R^7$ is independently H, alkyl, cycloalkyl, alkoxy, —OH, —SH, alkylthio, hydroxyalkyl, aryl, or heteroaryl; p is 0, or 1; q is 0, or 1; X is CO, or $SO_2$.

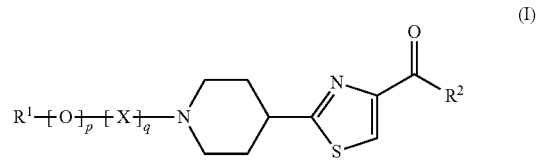

(I)

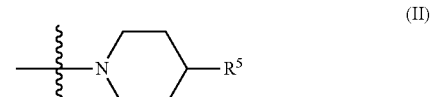

(II)

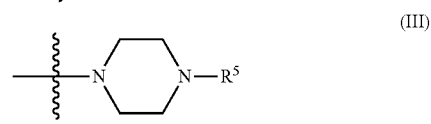

(III)

16 Claims, No Drawings

FOREIGN PATENT DOCUMENTS

| WO | 2005/003128 A1 | 1/2005 |
|---|---|---|
| WO | 2005/058887 | 6/2005 |
| WO | 2006/032322 A1 | 3/2006 |
| WO | 2004/058750 | 7/2006 |

OTHER PUBLICATIONS

Boger et al, "A New Class of Highly Cytotoxic Diketopiperazines", Biorganic & Medicinal Chemistry Letters 10 (2000) pp. 1019, 1020.

Lange et al, "Synthesis of Highly Potent and Selective Hetaryl Ureas as Integrin . . .", Biorganic & Medicinal Chemistry Letters 12 (2002) pp. 1379-1382.

El-Subbagh et al, 2,4-Disubstituted thiazoles II., Eur J. Med Chem (1996), 31. pp. 1017-1021.

Rao et al, "Synthesis of Noval Thiazole-Containing DNA Minor Groove Binding Oligopeptides Related to the Antiobiotic Distamycin" J. Org. Chem., vol. 55, No. 2, p. 728-737.

Kumar et al, "Synthesis and Antitumor Cytotoxicity Evaluation of Novel Thiazole-Containing Glycosylated Polyamides", Eur. J. Org. Chem, 2003, pp. 4842-4851.

Khalaf et al, "Distamycin Analogues with Enhances Lipophilicity: Synthesis and Antimicrobial Activity", J. Med. Chem., 2004, vol. 47, No. 8, pp. 2133-2156.

Wipf et al, "Total Synthesis of (−)-Muscoride A", J. Org. Chem. 1996, vol. 61, No. 19, pp. 6517-6522.

Boyce et al, "Naturally Occurring 4-Methylthiazolines. A Total Synthesis of (−)[4R, 4S']-Didehydromirabazole A", Tetrahedron, 1995 vol. 51, No. 26, pp. 7313-7320.

Parsons, Jr. et al, Total Synthesis of (−)-Thiangazole, a Naturally-Occurring HIV-1 Inhibitor, J. Org. Chem., 1994, vol. 59, No. 17, pp. 4733-4734.

Wipf et al, "Total Synthesis of (−)-Thiangazole and Structrally Related Polyazoles" J. Org. Chem, 1995 vol. 60, No. 22, pp. 7224-7229.

Franchetti et al, "A New C-Nucleoside Analogue of Tiazofurin Synthesis and Biological Evaluation . . .", Bioorg. Med. Chem. Lett. (2001) 11, pp. 67-69.

Hahnemann et al, "On the Reaction of Thiazole-2,4-diamines with Isothiocyanates . . .", Helvetica Chimica Acta (2003) vol. 86, pp. 1949-1965.

Coqueron et al, "Iterativer Aufbau von Oxazolringen uber a-Chlorglycinate . . ." Angew Chem. (2003)vol. 115, No. 12, pp. 1451-1454.

Wipf et al, "From Aziridines to Oxazolines and Thiazolines: The Heterocyclic Route to Thiangazole", Synlett, (1997) pp. 1-10.

Das et al, "Thromboxane A2/endoperoxide Receptor Antagonists: 1,3-Dioxane and 1,3-Dioxolane Analogs" Bioorganic & Medicinal Chemistry Ltrs, (1993)vol. 3, No. 6, pp. 1271-1276.

Herrmann et al, "Chemical Modification of Thiangazole A in the Oxazole and Styryl Region", Eur. J. Org., Chem. (1999), pp. 3381-3392.

European Patent Office Communication, Mar. 15, 2005.

International Search Report for PCT/EP2005/008261, Dated Oct. 11, 2005.

\* cited by examiner

HETEROCYCLIC NF-κB INHIBITORS

CROSS-REFERENCE TO RELATED APPLICATIONS

This is a U.S. National Phase of International Patent Application Serial No. PCT/EP2005/008261, filed Jul. 29, 2005 and claims priority to European Patent Application 04022363.8, filed Sep. 20, 2004 and U.S. Provisional Application 60/612,794, filed on Sep. 27, 2004. These aforementioned applications are incorporated by reference in their entireties.

FIELD OF THE INVENTION

The present invention relates to compounds of the general formula (I) or a salt or a physiologically functional derivative or a stereoisomer thereof, for use as a medicament. The compounds of the invention are exceptionally useful for the treatment of diseases associated with abnormal and hyperproliferation of cells in mammals, especially in humans. In particular, they are useful for the treatment of diseases characterized by a hyperproliferation of T-cells.

The present invention relates to compounds which are suitable for the therapy of diseases that can be treated by modulating cellular pathways in eukaryotes, e.g. cancer, immunological or inflammatory disorders, and viral infections, to further processes for the preparation of these compounds, and to their use.

The present invention also relates to novel heterocyclic compounds of the general formula (II) or (III) and salts thereof, to methods of using such compounds in treating NF-κB pathway associated disorders such as immunologic and oncologic disorders, and to pharmaceutical compositions containing such compounds.

T-cell homeostasis is critical for the maintenance of immune tolerance. Defects in T-cell homeostasis can lead to autoimmune pathology. Autoimmune diseases include a large spectrum of clinically distinct entities that share a common aetiology, a misguided, self-directed immune response.

This immune response can also be the consequence of an organ transplant.

Evidence suggests a prime role of T-cell reactivity in autoimmune diseases. Measuring proliferative responses in T-lymphocytes is a widely used assay to measure immune competence (Killestein, J. et al. *J. Neuroimmunol.* 133, 217-24, 2002).

We used a nonradioactive technique for the measurement of in vitro T-cell proliferation (Messele, T. et al. *Clinical and Diagnostic Laboratory Immunology* 687-692, 2000). Peripheral blood mononuclear cells (PBMCs) were isolated from human blood obtained from volunteer donators. PBMCs were isolated by centrifugation in ACCUSPIN tubes using HISTOPAQUE.

PBMCs were stimulated with PHA and cell proliferation was measured with a Roche calorimetric BromUridin incorporation ELISA kit.

Regulation of the immune response is controlled by a variety of signalling pathways such as T-cell or TNF receptor signalling (Chen, G. et al. *Science* 296, 1634-1635, 2002). To further characterize targets of compounds which we found active in the T-cell proliferation assay, we tested the compounds on their ability to inhibit the human proteasome.

The major neutral proteolytic activity in the cytosol and nucleus is the proteasome, a 20S (700 kDa) particle with multiple peptidase activities. The continual turnover of cellular proteins by the ubiquitin-proteasome pathway is used by the immune system to screen for the presence of abnormal intracellular proteins (Dantuma, N. P. et al. *Nat. Biotechnol.* 2000, 18(5), 538-43; Goldberg, A L. et al. *Nature* 357, 375, 1993).

The ubiquitin-proteasome pathway plays an essential role in the regulation of NF-κB activity, being responsible for the degradation of the inhibitor IκB-α. In order to be targeted for degradation by the proteasome, IκB-α must first undergo selective phosphorylation at serine residues 32 and 36, followed by ubiquitinylation (Chen, Z J. et al. *Cell* 84, 853-862, 1996; Brown, K. et al. *Science* 267, 1485, 1995).

NF-κB, a transcription factor, regulates the transcription of an important set of genes, involved in inflammatory responses (Baeuerle, P A. et al. *Cell* 87, 1, 13-20, 1996). Proteasome inhibitors block IκB-α degradation and NF-κB activation (Traeckner et al. *EMBO J.* 113, 5433, 1994).

Patents describing proteasome inhibitors have been described in reviews (Adams, J. et al. *Ann. Rev. Med. Chem.* 31, 279-288, 1996) and in U.S. Pat. Nos. 6,117,887, 5,834,487, WO 00/004954, WO 00/04954, WO 00/170204, WO 00/33654, WO 00/64863, WO 00/114324, WO 99/15183, WO 99/37666.

One such compound, named velcade (bortezomib), has been approved to treat multiple myeloma (Paramore, A. et al. *Nature Reviews,* 2, 611, 2003).

Here we describe novel chemical entities with proteasome inhibitory activity.

NF-κB (Nuclear Factor-κB) is an eucariotic transcription factor of the rel family, which is located in the cycloplasm in an inactive complex, as a homo- or heterodimer. Predominantly it exists as a heterodimer composed of p50 and p65 subunits, bound to inhibitory proteins of the IκB family, usually IκB-α (D. Thanos et al., *Cell* 80, 529, 1995). NF-κB is activated in response to different stimuli, among which inflammatory cytokines, UV radiation, phorbol esters, bacterial and viral infections. Stimulation triggers the release of NF-κB from IκB in consequence of the phosphorylation and the following degradation of the IκB-α protein (P. A. Baeuerle et al., *Annu. Rev. Immunol.* 12, 141, 1995) by the proteasome. Once it is set free, NF-κB translocates in the nucleus where it binds to the DNA at specific κB-sites and induces the transcription of a variety of genes encoding proteins involved in controlling the immune and inflammatory responses, amongst others interleukins, TNF-α, the NO-synthase and the cyclooxigenase 2 (S. Grimm et al., *J. Biochem.* 290, 297, 1993). Accordingly, NF-κB is considered an early mediator of the immune and inflammatory responses and it is involved in the control of cell proliferation and in the pathogenesis of various human diseases, such as rheumatoid arthritis (H. Beker et al., *Clin. Exp. Immunol.* 99, 325, 1995), ischemia (A. Salminen et al., *Biochem. Biophys. Res. Comm.* 212, 939, 1995), arteriosclerosis (A. S. Baldwin, *Annals Rev. Immunol.* 212, 649, 1996), as well as in the pathogenesis of AIDS.

Inhibition of NF-κB mediated gene transcription can be accomplished through inhibition of phosphorylation of the inhibitory protein IκB, inhibition of IκB degradation, inhibition of NF-κB (p50/p65) nuclear translocation, the inhibition of NF-κB-DNA binding or NF-κB-mediated DNA transcription (J. C. Epinat et al., *Oncogene* 18, 6896, 1999).

There are several compounds that are known to inhibit NF-κB mediated transcriptional activation. Several different natural products such as caffeic acid phenyl ester (1) (K. Natarajan et al., *Proc. Natl. Acad. Sci. USA,* 93, 9090, 1996), capsaicin (2) (S. Singh et al., *J. Immunol.* 157, 4412, 1996) and N-acetylcysteine (3) (R. Pinkus et al., *J. Biol. Chem.* 271, 13422, 1996) have been shown to block NF-κB activation (FIG. 1). Caffeic acid phenyl ester was shown to block NF-κB activation by TNF-α, phorbol ester, ceramide, hydrogen peroxide. This compound had no effect on TNF-induced IκB degradation but prevented the translocation of the p65 subunit of NF-κB to the nucleus. Capsaicin blocked TNF-α and phorbol mediated NF-κB activation. This compound also blocked degradation of IκB-α, and thus the nuclear translocation of NF-κB.

FIG. 1.

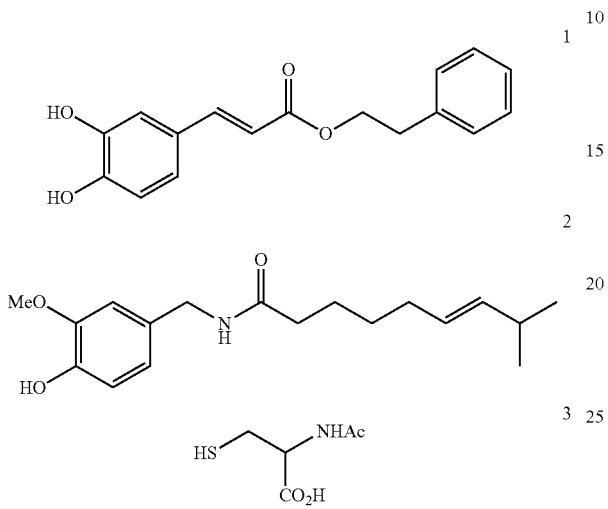

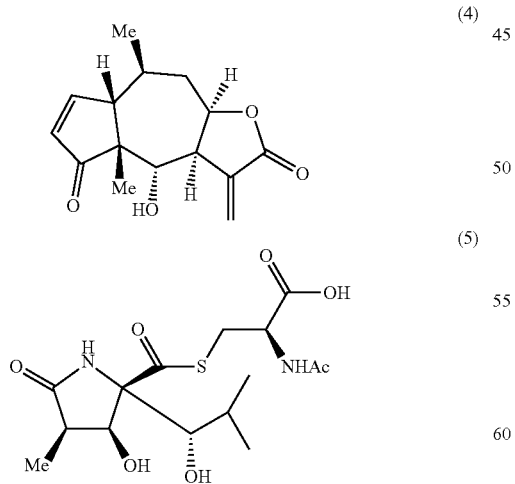

Helenalin (4), a sesquiterpene natural product, was shown to inhibit NF-κB activity by selectively alkylating the cysteine residue of the p65 subunit of NF-κB (G. Lyss et al., *J. Biol. Chem.* 273, 33508, 1998 and P. Rungeler et al., *Bioorg. Med. Chem.* 7, 2343, 1999) (FIG. 2). Helenalin, however, did not inhibit neither IκB degradation nor NF-κB translocation. Lactacystin (5), also a natural product, inhibits both, 20S and 26S proteasome (G. Fenteany et al., *Science* 268, 726, 1995) (FIG. 2). 26S proteasome is involved in degradation of phosphorylated IκB. This compound has inhibitory activity on trypsin-like, chymotrypsin-like and peptidylglutamylpeptide hydrolyzing activities.

FIG. 2.

Several synthetic compounds such as pyrrolidine dithiocarbamate (6), nicotinamide (7), and 3-chloroprocainamide (8) were shown to be inhibitors of NF-κB transcritional activation (R. W. Pero et al., *Mo. Cell. Biochem.* 193, 119, 1999) (FIG. 3). These compounds blocked lipopolysacharide-induced TNF-α production in mouse in a dose dependent manner. However, the exact site of activation of these compounds is not clear.

FIG. 3.

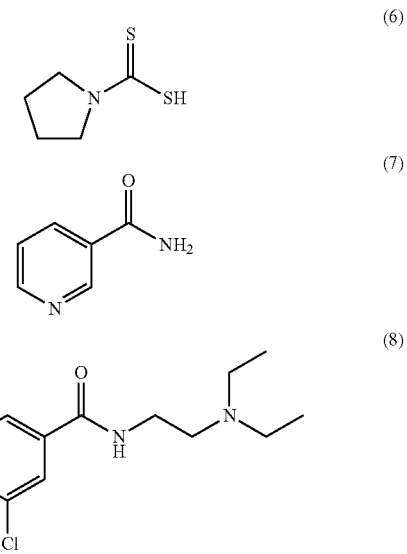

Celgene (Signal) introduced a novel class of quinazoline-pyrrole derivatives (9), which proved to be very potent inhibitors (up to 8 nM) of NF-κB mediated transcriptional activation (M. S. S. Palanki, *Curr. Med. Chem.* 9, 219, 2002).

FIG. 4.

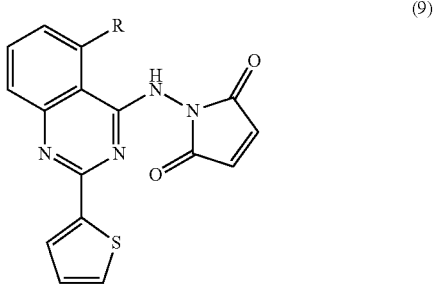

In WO 2001068648 a series of β-carbolines were claimed with IC50 values up to 150 nM for compound 10, which blocked TNFα-induced IκB phosphorylation and degradation in HeLa cells (FIG. 5). The same class was investigated by Millenium (A. B. Rabson, D. Weissmann, *Clin. Cancer Res.* 11, 2, 2005).

FIG. 5.

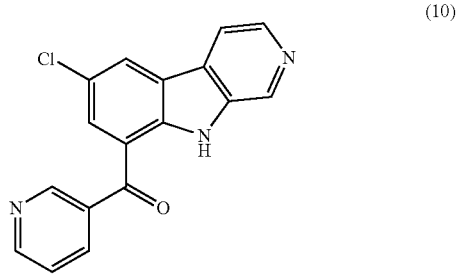

Patent WO 04066996 discloses a novel class of imidazolidine based compounds (11), which show 88% NF-κB inhibition at a concentration of 1 μM, with an $IC_{50}$ value of 0.3 μM (FIG. 6).

FIG. 6.

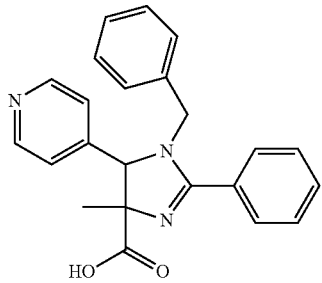
(11)

Presently only unsatisfactory therapies are established in this field, and therefore there still is a great need for new therapeutic agents that inhibit the NF-κB-pathway.

The novel compounds described herein are a new group of small molecule inhibitors, which show an outstanding inhibition of the NF-κB-pathway.

The object of the present invention is solved by the subject-matter of the independent claims. Further advantageous features, aspects and details of the invention are evident from the dependent claims, the description, the figures, and the examples of the present application.

The present invention relates to compounds of the general formula (I) or a salt or a physiologically functional derivative or a stereoisomer thereof,

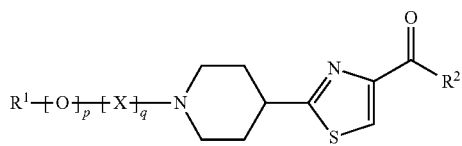
(I)

wherein
$R^1$ is independently hydrogen, alkyl, cycloalkyl, hydroxyalkyl, haloalkyl, haloalkyloxy, aryl, substituted aryl, heteroaryl, substituted heteroaryl, arylalkyl or substituted arylalkyl;
$R^2$ is independently —$NR^3R^4$,

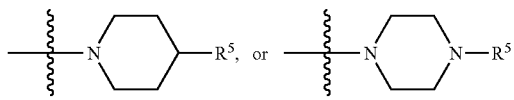

$R^3$ is independently alkyl, cycloalkyl, alkoxy, alkylamine, —OH, —SH, alkylthio, hydroxyalkyl, haloalkyl, haloalkyloxy, aryl or heteroaryl;
$R^4$ is independently alkyl, cycloalkyl, alkoxy, alkylamine, alkylthio, hydroxyalkyl, haloalkyl, haloalkyloxy, aryl or heteroaryl;
$R^5$ is independently H, $COR^6$, $CO_2R^6$, $SOR^6$, $SO_2R^6$, $SO_3R^6$, alkyl, cycloalkyl, alkoxy, —$NH_2$, alkylamine, —$NR^7COR^6$, halogen, —OH, —SH, alkylthio, hydroxyalkyl, haloalkyl, haloalkyloxy, aryl or heteroaryl;
$R^6$ is independently H, alkyl, cycloalkyl, —$NH_2$, alkylamine, aryl or heteroaryl;
$R^7$ is independently H, alkyl, cycloalkyl, alkoxy, —OH, —SH, alkylthio, hydroxyalkyl, aryl, or heteroaryl;
p is 0, or 1;
q is 0, or 1;
X is CO or $SO_2$;
an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkinyl group, which can optionally be substituted by one or more substituents R'; the $C_1$-$C_6$-alkyl, $C_2$-$C_6$-alkenyl and $C_2$-$C_6$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH($CH_3$)$_2$, —CH($CH_3$)—$C_2H_5$, —C($CH_3$)$_3$, —$C_5H_{11}$, —$C_6H_{13}$, —C(R')$_3$, —$C_2$(R')$_5$, —$CH_2$—C(R')$_3$, —$C_3$(R')$_7$, —$C_2H_4$—C(R')$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3$)$_2$, C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;
R' is independently H, —$CO_2R"$, —CONHR", —CR"O, —$SO_2NR"$, —NR"—CO-haloalkyl, —$NO_2$, —NR"—$SO_2$-haloalkyl, —NR"—$SO_2$-alkyl, —$SO_2$-alkyl, —NR"-CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
R" is independently H, haloalkyl, hydroxyalkyl, alkyl, cycloalkyl, aryl, heteroaryl or aminoalkyl;
a cycloalkyl group denotes a non-aromatic ring system containing three to eight carbon atoms, preferably four to eight carbon atoms, wherein one or more of the carbon atoms in the ring can be substituted by a group E, E being O, S, SO, $SO_2$, N, or NR", R" being as defined above; the $C_3$-$C_8$-cycloalkyl residue may be selected from the group comprising -cyclo- C₃H₅, -cyclo-C₄H₇, -cyclo-C₅H₉, -cyclo-C₆H₁₁, -cyclo-C₇H₁₃, -cyclo-C₈H₁₅, morpholine-4-yl, piperazinyl, 1-alkylpiperazine-4-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C(R¹⁰)₃, —CR¹⁰(R¹⁰')₂, —CR¹⁰(R¹⁰')R¹⁰'', —C₂(R¹⁰)₅, —CH₂—C(R¹⁰)₃, —CH₂—CR¹⁰(R¹⁰')₂, —CH₂—CR¹⁰(R¹⁰')R¹⁰'', —C₃(R¹⁰)₇, or —C₂H₄—C(R¹⁰)₃, wherein R¹⁰, R¹⁰', R¹⁰'' represent F, Cl, Br or I, preferably F;

a hydroxyalkyl group denotes an HO-alkyl group, the alkyl group being as defined above; an haloalkyloxy group denotes an alkoxy group which is substituted by one to five halogen atoms, the alkyl group being as defined above; the haloalkyloxy group is preferably a —OC(R¹⁰)₃, —OCR¹⁰(R¹⁰')₂, —OCR¹⁰(R¹⁰')R¹⁰'', —OC₂(R¹⁰)₅, —OCH₂—C(R¹⁰)₃, —OCH₂—CR¹⁰(R¹⁰')₂, —OCH₂—CR¹⁰(R¹⁰')R¹⁰'', —OC₃(R¹⁰)₇ or —OC₂H₄—C(R¹⁰)₃, wherein R¹⁰, R¹⁰', R¹⁰'' represent F, Cl, Br or I, preferably F;

a hydroxyalkylamino group denotes an (HO-alkyl)₂-N— group or HO-alkyl-NH— group, the alkyl group being as defined above;

an alkylamino group denotes an HN-alkyl or N-dialkyl group, the alkyl group being as defined above;

a halogen group is chlorine, bromine, fluorine or iodine;

an aryl group denotes an aromatic group having five to fifteen carbon atoms, which can optionally be substituted by one or more substituents R', where R' is as defined above; the aryl group is preferably a phenyl group, -o-C₆H₄—R', -m-C₆H₄—R', -p-C₆H₄—R', 1-naphthyl, 2-naphthyl, 1-anthracenyl or 2-anthracenyl;

a heteroaryl group denotes a 5- or 6-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 4-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzothiazolyl, quinazolinyl, quinoxazolinyl, quinolinyl, tetrahydroquinolinyl, isoquinolinyl, tetrahydrothieno[3,4-d]imidazol-2-one, pyrazolo[5,1-c][1,2,4]triazine, or tetrahydroisoquinolinyl group. This heterocyclic group can optionally be substituted by one or more substituents R', wherein R' is as defined above.

The invention also provides a pharmaceutical composition comprising a compound of formula (I), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs.

In addition, the present invention provides methods for preparing the compounds of the invention such as compounds of formula (I).

The compounds of formula (I) may be obtained via various methods.

Piperidin-4-yl-thiazole-4-carboxamide can be prepared by various methods described in the literature. One such example is the oxidation of the appropriate 2,5-dihydrothiazoles as described in *Houben-Weyl*, 2002, 730. The dihydrothiazoles can also synthesised by methods described in the same reference or described in You, S., Razavi, H., Kelly, J. W. *Angew. Chem.* 2003, 115, 87 or Katritzky, A R., Cai, C., Suzuki, K., Singh, S K. *J. Org. Chem.* 2004, 69, 811-814 and references in both papers. Alternative methods were described by Yasuchika, S. et. al. *Heterocycles*, Vol. 57, No. 5, 2002.

In a preferred embodiment of the invention, in the compounds of formula (I), R¹ is:

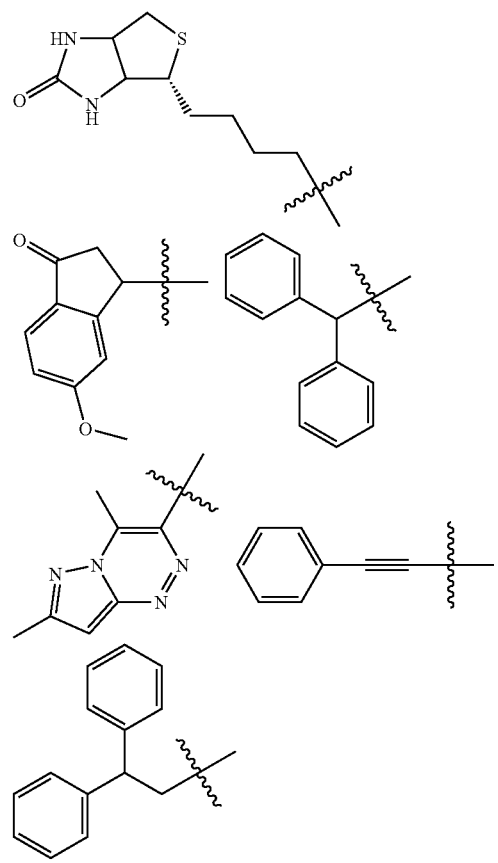

In a preferred embodiment of the invention, in the compounds of formula (I), R⁵ is:

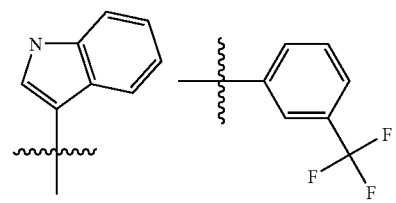

-continued

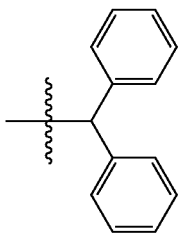

In another preferred embodiment, in the compounds of formula (I), $R^3$, $R^4$ and $R^7$ is H.

In a preferred embodiment of the invention, in the compounds of formula (I), $R^2$ is:

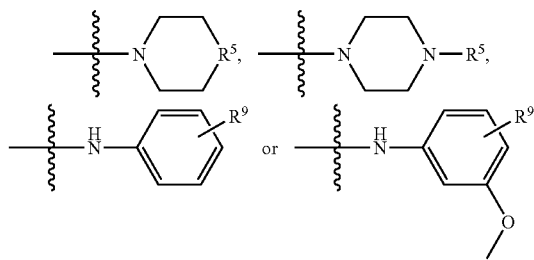

In a preferred embodiment of the invention, in the compounds of formula (I), $R^1$ is substituted aryl, p is 0, q is 1, X is CO, and $R^2$ is

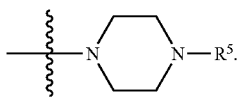

In a preferred embodiment of the invention, in the compounds of formula (I), $R^1$ is benzyl, p is 0, q is 0, and $R^2$ is

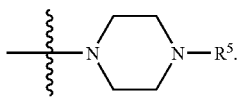

The present invention also relates to compounds of the general formula (III) or a salt or a physiologically functional derivative, or a stereoisomer thereof,

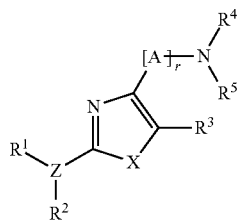

(III)

wherein
$R^1$ is $-C(O)R^7$, $-C(O)CHR^7R^8$, $-C(O)NR^7R^8$, $-C(O)OR^7$, $-R^7C(O)R^8$, $-C(S)R^7$, or $R^1$ and $R^2$ together with the N-atom or the C-atom to which they are attached form a 3 to 8 membered ring, wherein at least one or more of the carbon atoms in the ring is a heteroatom like O, N, S and the ring can be substituted by $R^9$;

$R^2$ is H, alkyl, cycloalkyl, heterocycloalkyl, haloalkyl, hydroxyalkyl, hydroxyalkylamino, alkylamino, heteroaryl, alkylaryl, aryl or $R^2$ is absent in the case Z forms a ring together with $R^1$;

$R^3$ is H, $-C(O)NR^aR^b$, halogen, alkyl, haloalkyl, aryl or heteroaryl;

$R^4$ is H, halogen, alkyl, $-C(NR^7)NR^7R^8$, $-(CH_2)_p$aryl, $-(CH_2)_pNR^7R^8$, $-C(O)NR^7R^8$, $-N=CR^7R^8$, $-NR^7C(O)R^8$, cycloalkyl, heterocycloalkyl, haloalkyl, hydroxyalkyl, hydroxyalkylamino, alkylamino, heteroaryl, alkylaryl, or aryl;

$R^5$ is H, halogen, alkyl, $-C(NR^7)NR^7R^8$, $-(CH_2)_p$aryl, $-(CH_2)_pNR^7R^8$, $-C(O)NR^7R^8$, $-N=CR^7R^8$, $-NR^7C(O)R^8$, cycloalkyl, heterocycloalkyl, haloalkyl, hydroxyalkyl, hydroxyalkylamino, alkylamino, heteroaryl, alkylaryl, or aryl;

$R^a$ is H, halogen, alkyl, $-C(NR^7)NR^7R^8$, $-(CH_2)_p$aryl, $-(CH_2)_pNR^7R^8$, $-C(O)NR^7R^8$, $-N=CR^7R^8$, $-NR^7C(O)R^8$, cycloalkyl, heterocycloalkyl, haloalkyl, hydroxyalkyl, hydroxyalkylamino, alkylamino, heteroaryl, alkylaryl, or aryl;

$R^b$ independently represents H, $-CN$, $-OH$, $-SH$, $-CO_2R^{4'}$, $-C(O)R^{4'}$, $-SO_2NR^{4'}$, $-NR^4R^{5'}$, $-C(O)NR^7R^8$, $-SO_2$-alkyl, $-SO_2R^{4'}$, $SO_3R^{4'}$, $-N=CR^4R^{5'}$, $-NR^{4'}C(O)R^{4''}$, $-NR^{4''}-CO$-haloalkyl, $-NO_2$, $-NR^{4'}-SO_2$-haloalkyl, $-NR^{4'}-SO_2$-alkyl, $-NR^{4'}-CO$-alkyl, $-NR^{4'}(CH_2)_p$heterocycle, alkyl, cycloalkyl, alkylamino, alkoxy, alkylthio, halogen, haloalkyl, haloalkyloxy, $-O(CH_2)_p[O(CH_2)_p]_qOCH_3$, $-C(NR^{4''})NR^{4'}$benzimidazolyl, $-C(NR^{4''})NR^{4'}$benzthiazolyl, $-C(NR^{4''})NR^{4'}$benz-oxazolyl, hydroxyalkyl, hydroxycycloalkyl, hydroxyalkylamino, aryl, arylalkyl or a heterocycle;

$R^{4'}$, $R^{4''}$, $R^{5'}$ independently are H, halogen, alkyl, $-C(NR^7)NR^7R^8$, $-(CH_2)_p$aryl, haloalkyl, $-CH_2)_pNR^7R^8$, $-C(O)NR^7R^8$, $-N=CR^7R^8$, $-NR^7C(O)R^8$, cycloalkyl, heterocycloalkyl, hydroxyalkyl, hydroxyalkylamino, alkylamino, heteroaryl, alkylaryl, or aryl;

$R^7$, $R^{7'}$, $R^8$ independently are H, halogen, alkyl, cycloalkyl, heterocycloalkyl, haloalkyl, hydroxyalkyl, hydroxyalkylamino, alkylamino, heteroaryl, alkylaryl, or aryl;

A is CO or $SO_2$;
X is $NR^{2'}$, O, S, or $CR^{2'}$;
Z is N or $CR^{2'}$; if Z is CH then X is O or $NR^{2'}$
$R^{2'}$ is H, alkyl, $-C(O)NR^2$, $-C(O)R^b$, cycloalkyl, heterocycloalkyl, haloalkyl, hydroxyalkyl, hydroxyalkylamino, alkylamino, heteroaryl, alkylaryl, or aryl;
p is 1 to 6;
q is 1 to 6;
r is 0, or 1;

$R^9$ independently represents H, $-CN$, $-OH$, $-SH$, alkoxy, alkylthio, $-CO_2R^{4'}$, $-C(O)R^{4'}$, $-C(O)NR^7R^8$, $-SO_2NR^{4'}$, $-NR^4R^{5'}$, $-SO_2$-alkyl, $-SO_2R^{4'}$, $SO_3R^{4'}$, $-N=CR^4R^{5'}$, $-NR^{4'}C(O)R^{4''}$, $-NR^{4'}-CO$-haloalkyl, $-NO_2$, $-NR^{4'}-SO_2$-haloalkyl, $-NR^{4'}-SO_2$-alkyl, $-NR^{4'}-CO$-alkyl, $-NR^{4'}(CH_2)_p$heterocycle, alkyl, hydroxyalkyl, cycloalkyl, alkylamino, $-O(CH_2)_p[O(CH_2)_p]_qOCH_3$, $-C(NR^{4''})NR^{4'}$benzimidazolyl, $-C(NR^{4''})NR^{4'}$benzthiazolyl, $-C(NR^{4''})NR^{4'}$benzoxazolyl, hydroxycycloalkyl, hydroxyalkylamino, halogen, haloalkyl, haloalkyloxy, aryl, arylalkyl or a heterocycle;

R$^{4'}$, R$^{4''}$, R$^{5'}$ independently are H, halogen, alkyl, —C(NR$^7$)NR$^7$R$^8$, —(CH$_2$)$_p$aryl, hydroxyalkyl, —CH$_2$)$_p$NR$^7$R$^8$, —C(O)NR$^7$R$^8$, —N═CR$^7$R$^8$, —NR$^7$C(O)R$^8$, cycloalkyl, heterocycloalkyl, haloalkyl, hydroxyalkylamino, alkylamino, heteroaryl, alkylaryl, or aryl;

wherein an alkyl group, if not stated otherwise, denotes a linear or branched C$_1$-C$_6$-alkyl, preferably a linear or branched chain of one to six carbon atoms, a linear or branched C$_2$-C$_6$-alkenyl or a linear or branched C$_2$-C$_6$-alkynyl group, which can be substituted by one or more substituents R$^9$; R$^9$ being defined as above.

a heterocycle denotes a heterocycloalkyl group or a heteroaryl group;

a cycloalkyl group denotes a non-aromatic ring system containing three to eight carbon atoms, preferably four to eight carbon atoms, wherein one or more of the carbon atoms in the ring can be substituted by a group R$^9$ being as defined above; the C$_3$-C$_8$-cycloalkyl residue may be selected from the group comprising -cyclo-C$_3$H$_5$, -cyclo-C$_4$H$_7$, -cyclo-C$_5$H$_9$, -cyclo-C$_6$H$_{11}$, -cyclo-C$_7$H$_{13}$, -cyclo-C$_8$H$_{15}$;

a heterocycloalkyl group denotes a non-aromatic ring system containing two to ten carbon atoms and at least one heteroatom like O, N, or S, wherein one or more of the carbon atoms in the ring can be substituted by R$^9$ being as defined above; preferred heterocycloalkyl groups are morpholine-4-yl, piperazinyl, 1-alkylpiperazine-4-yl, piperidinyl, pyrrolidinyl, azepane-1-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$C(R$^{10}$)$_3$, —CH$_2$CR$^{10}$(R$^{10'}$)$_2$, —CH$_2$CR$^{10}$(R$^{10'}$)R$^{10''}$, —C$_3$(R$^{10}$)$_7$, or —C$_2$H$_4$C(R$^{10}$)$_3$, wherein R$^{10}$, R$^{10'}$, R$^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$C(R$^{10}$)$_3$, —OCH$_2$CR$^{10}$(R$^{10'}$)$_2$, —OCH$_2$CR$^{10}$(R$^{10'}$)R$^{10''}$, —OC$_3$(R$^{10}$)$_7$, or —OC$_2$H$_4$C(R$^{10}$)$_3$, wherein R$^{10}$, R$^{10'}$, R$^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R$^9$, where R$^9$ is as defined above; the aryl group is preferably a phenyl group, -o-C$_6$H$_4$—R$^9$, -m-C$_6$H$_4$—R$^9$, -p-C$_6$H$_4$—R$^9$, 1-naphthyl, 2-naphthyl, 1-anthracenyl or 2-anthracenyl, R$^9$ being as defined above;

a heteroaryl group denotes a 5- to 10-membered aromatic heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzthiazolyl, benzoxazolyl, quinazolinyl, quinoxazolinyl, quinolinyl, tetrahydroquinolinyl, isoquinolinyl, or tetrahydroisoquinolinyl group. This heterocyclic group or the fused ring can both be substituted independently by one or more substituents R$^9$, wherein R$^9$ is as defined above;

a alkylaryl or arylalkyl group denotes an alkyl group (see def. 'alkyl'), which is bound to an aryl fragment (see def. 'aryl') via a single bond. The linkage to the central moiety might occur over the alkyl part or the aryl part.

The present invention relates also to compounds of the general formula (II) or a salt or a physiologically functional derivative, or a stereoisomer thereof,

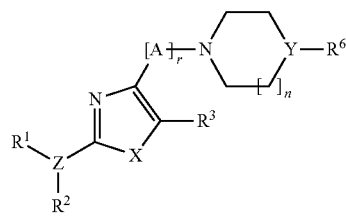

(II)

wherein

R$^1$ is —C(O)R$^7$, —C(O)CHR$^7$R$^8$, —C(O)NR$^7$R$^8$, —C(O)OR$^7$, —R$^7$C(O)R$^8$, —C(S)R$^7$, or R$^1$ and R$^2$ together with the N-atom or the C-atom to which they are attached form a 3 to 8 membered ring, wherein at least one or more of the carbon atoms in the ring is a heteroatom like O, N, S and the ring can be substituted by R$^9$;

R$^2$ is H, alkyl, cycloalkyl, heterocycloalkyl, haloalkyl, hydroxyalkyl, hydroxyalkylamino, alkylamino, heteroaryl, alkylaryl, aryl or R$^2$ is absent in the case Z forms a ring together with R$^1$;

R$^3$ is H, —C(O)NR$^4$R$^9$, halogen, alkyl, haloalkyl, aryl or heteroaryl;

R$^6$ is H, halogen, —C(O)R$^7$, —C(O)CHR$^7$R$^8$, —C(O)NR$^7$R$^8$, —C(O)OR$^7$, —R$^7$C(O)R$^8$, —C(S)R$^7$, —C(NR$^7$)NR$^7$R$^8$, —(CH$_2$)$_p$aryl, —(CH$_2$)$_p$NR$^7$R$^8$, —C(O)NR$^7$R$^8$, —N═CR$^7$R$^8$, —NR$^7$C(O)R$^7$, alkyl, cycloalkyl, heterocycloalkyl, haloalkyl, hydroxyalkyl, hydroxyalkylamino, alkylamino, heteroaryl, alkylaryl, or aryl;

R$^7$, R$^{7'}$, R$^8$ independently are H, halogen, alkyl, cycloalkyl, heterocycloalkyl, haloalkyl, hydroxyalkyl, hydroxyalkylamino, alkylamino, —NHaryl, heteroaryl, alkylaryl, or aryl;

A is CO or SO$_2$;

X is NR$^{2'}$, O, S, or CR$^{2'}$;

Y is N, O, or CR$^{2'}$;

Z is N or CR$^{2'}$; if Z is CH then X is O or NR$^{2'}$

R$^{2'}$ is H, alkyl, —C(O)NR$^2$, —C(O)R$^b$, cycloalkyl, heterocycloalkyl, haloalkyl, hydroxyalkyl, hydroxyalkylamino, alkylamino, heteroaryl, alkylaryl, or aryl;

n is 0 to 2;

p is 1 to 6;

q is 1 to 6;

r is 0, 1;

R$^9$ independently represents H, —CN, —OH, —SH, —CO$_2$R$^{4'}$, —C(O)R$^{4'}$, —C(O)NR$^7$R$^8$, —SO$_2$NR$^{4'}$, —NR$^{4'}$R$^{5'}$, —SO$_2$-alkyl, —SO$_2$R$^{4'}$, SO$_3$R$^{4'}$, —N═CR$^{4'}$R$^{5'}$, —NR⁴'C(O)R⁴''', —NR⁴'—CO-haloalkyl, —NO₂, —NR⁴'—SO₂-haloalkyl, —NR⁴'—SO₂-alkyl, —NR⁴'—CO-alkyl, —NR⁴'(CH₂)$_p$heterocycle, alkyl, cycloalkyl, alkylamino, alkoxy, alkylthio, —O(CH₂)$_p$[O(CH₂)$_p$]$_q$OCH₃, —C(NR⁴'')NR⁴''benzimidazolyl, —C(NR⁴'')NR⁴''benzthiazolyl, —C(NR⁴'')NR⁴''benzoxazolyl, hydroxyalkyl, hydroxycloalkyl, hydroxyalkylamino, halogen, haloalkyl, haloalkyloxy, aryl, arylalkyl or a heterocycle;

R⁴', R⁴'', R⁵' independently are H, halogen, alkyl, —C(NR⁷)NR⁷R⁸, —(CH₂)$_p$aryl, —CH₂)$_p$NR⁷R⁸, —C(O)NR⁷R⁸, —N═CR⁷R⁸, —NR⁷C(O)R⁸, cycloalkyl, heterocycloalkyl, haloalkyl, hydroxyalkyl, hydroxyalkylamino, alkylamino, heteroaryl, alkylaryl, or aryl;

wherein an alkyl group, if not stated otherwise, denotes a linear or branched C₁-C₆-alkyl, preferably a linear or branched chain of one to six carbon atoms, a linear or branched C₂-C₆-alkenyl or a linear or branched C₂-C₆-alkynyl group, which can be substituted by one or more substituents R⁹; R⁹ being defined as above.

a heterocycle denotes a heterocycloalkyl group or a heteroaryl group;

a cycloalkyl group denotes a non-aromatic ring system containing three to eight carbon atoms, preferably four to eight carbon atoms, wherein one or more of the carbon atoms in the ring can be substituted by a group R⁹ being as defined above; the C₃-C₈-cycloalkyl residue may be selected from the group comprising -cyclo-C₃H₅, -cyclo-C₄H₇, -cyclo-C₅H₉, -cyclo-C₆H₁₁, -cyclo-C₇H₁₃, -cyclo-C₈H₁₅;

a heterocycloalkyl group denotes a non-aromatic ring system containing two to ten carbon atoms and at least one heteroatom like O, N, or S, wherein one or more of the carbon atoms in the ring can be substituted by R⁹ being as defined above; preferred heterocycloalkyl groups are morpholine-4-yl, piperazinyl, 1-alkylpiperazine-4-yl, piperidinyl, pyrrolidinyl, azocane-1-yl;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above;

an haloalkyl group denotes an alkyl group which is substituted by one to five halogen atoms, the alkyl group being as defined above; the haloalkyl group is preferably a —C(R¹⁰)₃, —CR¹⁰(R¹⁰')₂, —CR¹⁰(R¹⁰')R¹⁰'', —C₂(R¹⁰)₅, —CH₂C(R¹⁰)₃, —CH₂CR¹⁰(R¹⁰')₂, —CH₂CR¹⁰(R¹⁰')R¹⁰'', —C₃(R¹⁰)₇, or —C₂H₄C(R¹⁰)₃, wherein R¹⁰, R¹⁰', R¹⁰'' represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R¹⁰)₃, —OCR¹⁰(R¹⁰')₂, —OCR¹⁰(R¹⁰')R¹⁰'', —OC₂(R¹⁰)₅, —OCH₂C(R¹⁰)₃, —OCH₂CR¹⁰(R¹⁰')₂, —OCH₂CR¹⁰(R¹⁰')R¹⁰'', —OC₃(R¹⁰)₇, or —OC₂H₄C(R¹⁰)₃, wherein R¹⁰, R¹⁰', R¹⁰'' represent F, Cl, Br or I, preferably F;

a hydroxyalkylamino group denotes an (HO-alkyl)₂-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R⁹, where R⁹ is as defined above; the aryl group is preferably a phenyl group, -o-C₆H₄—R⁹, -m-C₆H₄—R⁹, -p-C₆H₄—R⁹, 1-naphthyl, 2-naphthyl, 1-anthracenyl or 2-anthracenyl, R⁹ being as defined above;

a heteroaryl group denotes a 5- to 10-membered aromatic heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, 2-indolyl, 3-indolyl, 2-indolinyl, 3-indolinyl, benzo[b]furanyl, benzo[b]thiophenyl, benzimidazolyl, benzthiazolyl, benzoxazolyl, quinazolinyl, quinoxazolinyl, quinolinyl, tetrahydroquinolinyl, isoquinolinyl, or tetrahydroisoquinolinyl group. This heterocyclic group or the fused ring can both be substituted independently by one or more substituents R⁹, wherein R⁹ is as defined above;

a alkylaryl or arylalkyl group denotes an alkyl group (see def. 'alkyl'), which is bound to an aryl fragment (see def. 'aryl') via a single bond. The linkage to the central moiety might occur over the alkyl part or the aryl part.

A preferred embodiment of the invention, in the compounds of formula (III), are compounds of the formula (IIIa),

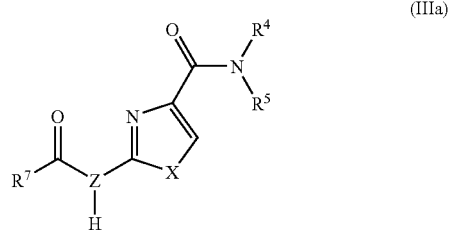

(IIIa)

wherein

R¹ is COR⁷; R² and R³ is H; A is CO;
R⁴, R⁵, R⁷ are defined as above; r is 1;
X is O or S; and Z is as defined as above.

Another preferred embodiment of the invention, in the compounds of formula (III), are compounds of the formula (IIIa), with R⁷═—NH-aryl.

Another preferred embodiment of the invention, in the compounds of formula (III), are compounds of the formula (IIIb),

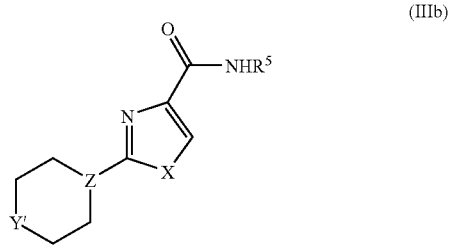

(IIIb)

wherein

R⁴ and R³ is H; A is CO; R⁵ is defined as above; X is O or S;
r is 1;
Z forms together with R¹ a 6-membered ring and R² is absent;
if Z is N then X is O or S, or if Z is CR²', X is O;
Y' is O or NR²', R²' is as defined above;

Another preferred embodiment of the invention, in the compounds of formula (III), are compounds of the formula (IIIc),

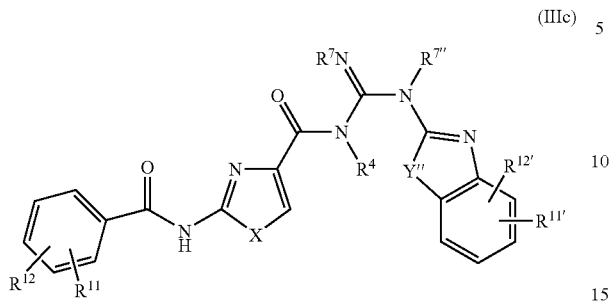

(IIIc)

wherein
$R^1$ is $COR^7$; wherein $R^7$ is phenyl and $R^{11}$, $R^{12}$ independently represent H, —CN, —OH, —SH, —$CO_2R^{4'}$, —$C(O)R^{4'}$, —$SO_2NR^{4'}$, —$NR^{4'}R^{5'}$, —$SO_2$-alkyl, —$SO_2R^{4'}$, $SO_3R^{4'}$, —$N=CR^{4'}R^{5'}$, —$NR^{4'}C(O)R^{4''}$, —$NR^{4'}$—CO-haloalkyl, —$NO_2$, —$NR^{4'}$—$SO_2$-haloalkyl, —$NR^{4'}$—$SO_2$-alkyl, —$NR^{4'}$—CO-alkyl, —$NR^{4'}(CH_2)_p$heterocycle, alkyl, cycloalkyl, alkylamino, alkoxy, alkylthio, —$O(CH_2)_p[O(CH_2)_p]_qOCH_3$, —$C(NR^{4''})NR^{4'}$benzimidazolyl, —$C(NR^{4''})NR^{4'}$benzthiazolyl, —$C(NR^{4''})NR^{4'}$benzoxazolyl hydroxyalkyl, hydroxycycloalkyl, hydroxyalkylamino, halogen, haloalkyl, haloalkyloxy, aryl, arylalkyl or a heterocycle; and $R^{4'}$, $R^{4''}$, $R^{5'}$ are defined as above;
r is 1; Z is N, $R^2$ and $R^3$ is H; X is O or S, A is CO;
$R^4$ is defined as above, $R^5$ is $C(NR^7)NR^{7'}R^8$,
$R^7$ and $R^{7'}$ are defined as above, $R^8$ is a heterocycloalkyl wherein Y" is O, S or $NR^{2'}$ and $R^{11'}$, $R^{12'}$ independently represents H, —CN, —OH, —SH, —$CO_2R^{4'}$, —$C(O)R^{4'}$, —$SO_2NR^{4'}$, —$NR^{4'}R^{5'}$, —$SO_2$-alkyl, —$SO_2R^{4'}$, $SO_3R^{4'}$, —$N=CR^{4'}R^{5'}$, —$NR^{4'}C(O)R^{4''}$, —$NR^{4'}$—CO-haloalkyl, —$NO_2$, —$NR^{4'}$—$SO_2$-haloalkyl, —$NR^{4'}$—$SO_2$-alkyl, —$NR^{4'}$—CO-alkyl, —$NR^{4'}(CH_2)_p$heterocycle, alkyl, cycloalkyl, alkylamino, alkoxy, alkylthio, —$O(CH_2)_p[O(CH_2)_p]_qOCH_3$, —$C(NR^{4''})NR^{4'}$-benzimidazolyl, —$C(NR^{4''})NR^{4'}$benzthiazolyl, —$C(NR^{4''})NR^{4'}$benzoxazolyl hydroxyalkyl, hydroxycycloalkyl, hydroxyalkylamino, halogen, haloalkyl, haloalkyloxy, aryl, arylalkyl or a heterocycle; and $R^{4'}$, $R^{4''}$, $R^{5'}$ are defined as above;

A more preferred embodiment of the invention, in the compounds of formula (III), are compounds of the formula (IIId),

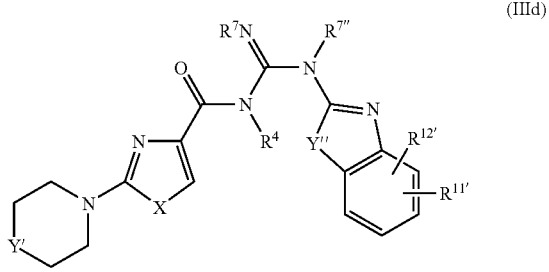

(IIId)

wherein
Z forms together with $R^1$ a 6-membered ring and $R^2$ is absent;
Z is N, and $R^3$ is H; X is O or S, A is CO;
$R^4$ is defined as above, $R^5$ is $C(NR^7)NR^{7'}R^8$,
$R^7$ and $R^{7'}$ are defined as above,
$R^8$, Y" and $R^{11'}$, $R^{12'}$ are defined as above under formula (IIIc),
r is 1; Y' is O or $NR^{2'}$ and $R^{2'}$ is as defined above.

Another more preferred embodiment of the invention, in the compounds of formula (III), are compounds of the formula (IIIe),

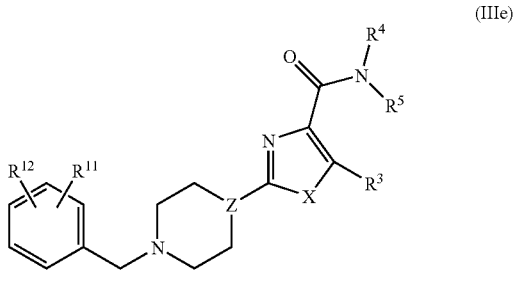

(IIIe)

wherein
Z forms together with $R^1$ a 6-membered ring and $R^2$ is absent;
r is 1; $R^3$, $R^4$ and $R^5$ are defined as above, A is CO; X is O or S,
$R^{11}$ and $R^{12}$ are defined as above under formula (IIIc), and if Z is N, X is O or S, if Z is CH, X is O.

Another more preferred embodiment of the invention, in the compounds of formula (III), are compounds of the formula (IIIf),

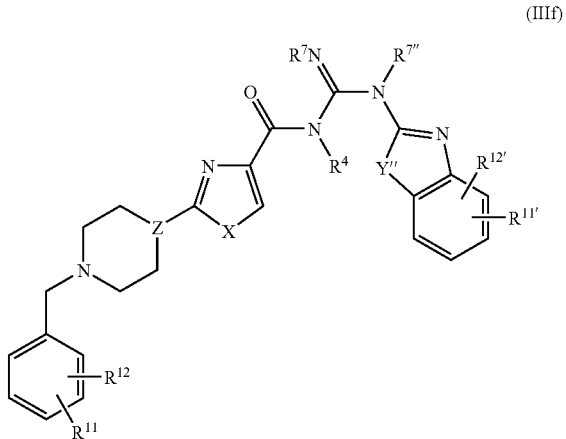

(IIIf)

wherein
Z forms together with $R^1$ a 6-membered ring and $R^2$ is absent;
Z is N or CH, and $R^3$ is H; X is O or S, A is CO;
$R^4$ is defined as above, $R^5$ is $C(NR^7)NR^{7'}R^8$,
$R^7$ and $R^{7'}$ are defined as above,
$R^8$, Y" and $R^{11'}$, $R^{11'}$, $R^{12}$, $R^{12'}$ are defined as above under formula (IIIc),
r is 1; Y' is O or $NR^{2'}$ and $R^{2'}$ is as defined above.

A preferred embodiment of the invention, in the compounds of formula (II), are compounds of the formula (IIa),

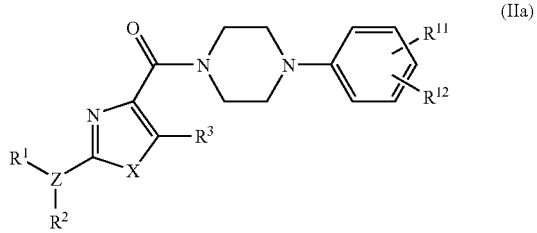

(IIa)

wherein
$R^1$ and $R^2$ are defined as above, Z is defined as above.
r is 1; A is CO; X is O or S, $R^3$ is H, Y is $NR^{2'}$ wherein $R^{2'}$ is phenyl and $R^{11}$ and $R^{12}$ are defined as above under formula (IIIc).

A more preferred embodiment of the invention, in the compounds of formula (II), are compounds of the formula (IIb),

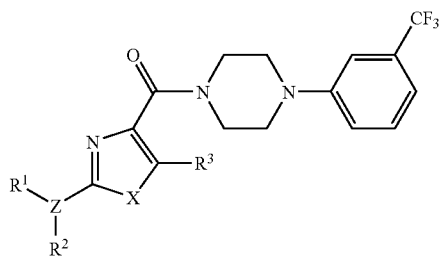
(IIb)

wherein
R¹ and R² are defined as above, Z is defined as above.
r is 1; A is CO; X is O or S, R³ is H,
Y is NR²'wherein R²' is phenyl and R¹¹ is H and R¹² is CF₃.

Another more preferred embodiment of the invention, in the compounds of formula (II), are compounds of the formula (IIc),

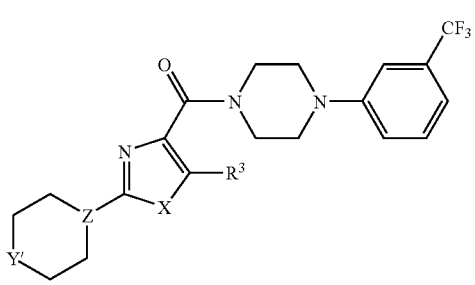
(IIc)

wherein
Z forms together with R¹ a 6-membered ring and R² is absent;
A is CO;
r is 1; X is O or S, R³ is H, Y' is NR²'.

Another more preferred embodiment of the invention, in the compounds of formula (II), are compounds of the formula (IId),

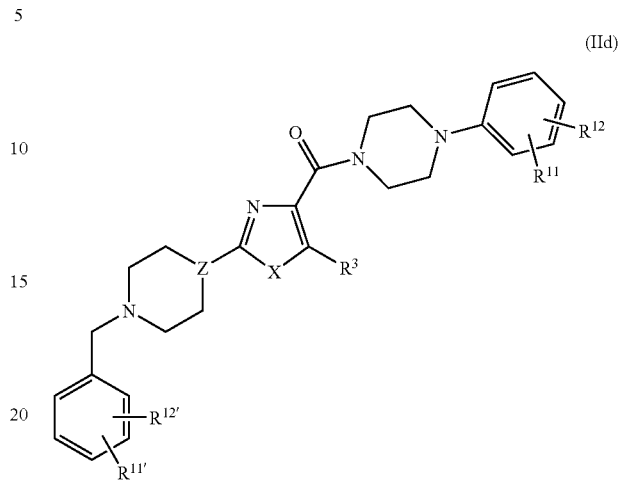
(IId)

wherein
Z is defined as above;
R³ is H, Y' is NR²'. R²' is as defined above;
R¹¹, R¹¹' and R¹², R¹²' are defined as above.

The compounds of formula (III) and (II) may be obtained via various methods. One possibility for the synthesis of compounds of formula (IIIa, c and IIa, b) (see scheme 1) comprises a step of reacting a compound of formula (V) with a compound of formula (VI) under classical amide coupling conditions, like e.g. HBTU, iPr₂NEt, DMF, 0° C. to r.t. to obtain intermediate (VII). Another alternative for this step might be the reaction of (V) with the corresponding acid chloride of (VI) to yield (VII). In a second step, compound (VII) is saponified with a 1 M NaOH solution, obtaining the expected acid (VIII) in almost quantitative yield. This step could be realized under acidic conditions as well. Finally, another amide coupling step (with primary or secondary amines), which works similarity to step 1 described above, completes the synthesis for compounds of type (IIIa, c and IIa, and b).

Scheme 1 Synthesis of derivatives of type (IIIa, c) and (IIa, b)

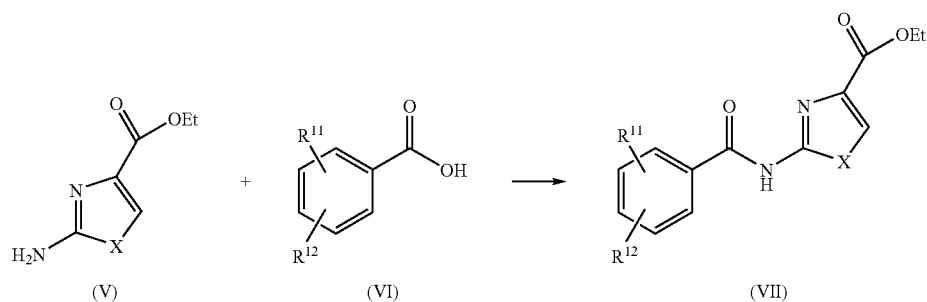

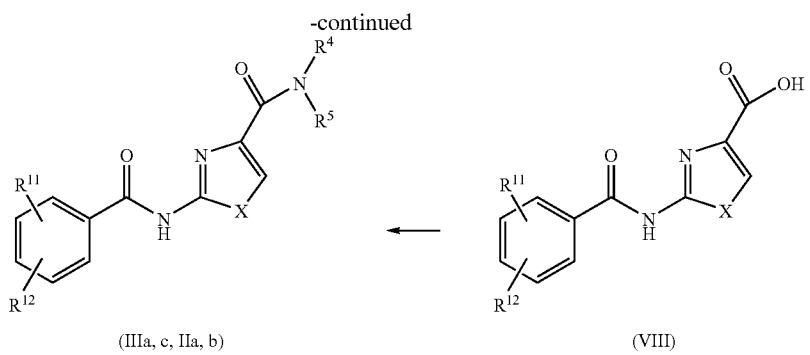

(IIIa, c, IIa, b)     (VIII)

Compounds dealing with structure (IIIb, d, e, f) and (IIc, d) can be synthesized according to the procedure displayed in scheme 2. Herein, a heterocycle (IX) is reacted with a bromocompound (X), by means of a nucleophilic substitution reaction, to gain a bicyclic ester (XI), which is then saponified under standard and well-known conditions to acid (XII), completing the synthesis with another coupling step as described in scheme 1 above.

Scheme 2 Synthesis of derivatives of type (IIIb, d, e, f) and (IIc, d), with Z = N

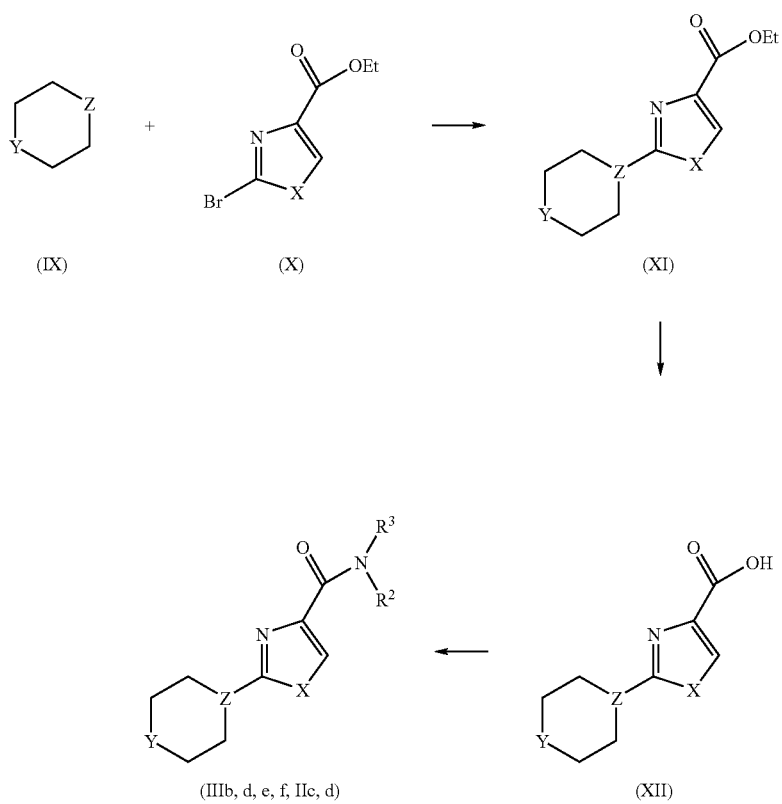

In case of Z=CH, structure (IIIb, d, e, f) and (IIc, d) type compounds can easily be synthesized following a protocol outlined in scheme 3, wherein a heterocycle (XIII) is converted to compound (XV) by a cyclokondensation step. After saponification, (XVI) is coupled with an amine to yield the desired product (IIIb, d, e, f) or (IIc, d).

Scheme 3 Synthesis of derivatives of type (IIIb, d, e, f) and (IIc, d), with Z = CH

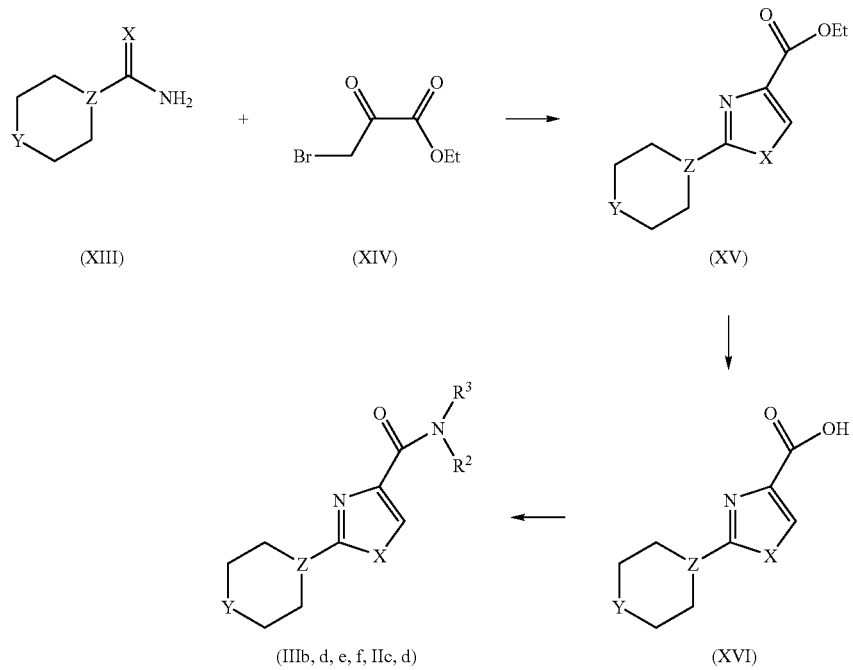

The compounds of the formula (I), (II) or (III) to be used according to the invention can form salts with inorganic or organic acids or bases. Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluene-sulfonic acid and others. Such salts can be produced by methods known to someone of skill in the art and described in the prior art.

Other salts like oxalate derived from oxalic acid, which is not considered as pharmaceutically acceptable can be appropriate as intermediates for the production of compounds of the formula (I), (II) or (III) or a pharmaceutically acceptable salt thereof or physiologically functional derivative or a stereoisomer thereof.

The invention also provides a pharmaceutical composition comprising a compound of formula (I), (II) or (III), in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves ('prodrugs') but which are transformed into their pharmaceutical active form in vivo, i.e. in the subject to which the compound is administered.

The compounds according to the invention and medicaments prepared therewith are generally useful for the treatment of cell proliferation disorders, for the treatment or prophylaxis of immunological diseases and conditions (as for instance inflammatory diseases, neuroimmunological diseases, autoimmune diseases or other).

The compounds of the present invention are useful for the treatment of diseases which are caused by malignant cell proliferation, such as all forms of solid tumors, leukemias and lymphomas. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, cervical, and ovarian, melanoma, astrocytoma, small cell lung cancer, glioma, basal and squameous cell carcinoma, sarcomas as Kaposi's sarcoma and osteosarcoma) or for the treatment of diseases which are cured or relieved by the inhibition of one or several kinases and/or phosphatases.

"Treatment" according to the present invention is intended to mean complete or partial healing of a disease, or alleviation of a disease or stop of progression of a given disease.

Thus, in one embodiment, the invention relates to the use of the compounds of the formula (I), (II), and (III) or a pharmaceutically acceptable salt or physiologically functional derivative or a stereoisomer thereof if desired with appropriate adjuvants and additives for the production of a medicament for the treatment or prevention of a disease characterized by hyperproliferation of keratinocytes and/or T cells, especially inflammatory disorders and immune disorders, preferably selected from the group consisting of Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, autoimmune hemolysis, Bechet's disease, Boeck's disease, inflammatory bowel disease, Burkitt's lymphoma, Crohn's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, autoimmune demyelinating diseases, Dupuytren's contracture, encephalomyelitis, encephalomyelitis allergica, endophthalmia phacoanaphylactica, enteritis allergica, autoimmune enteropathy syndrome, erythema nodosum leprosum, idiopathic facial paralysis, chronic fatigue syndrome, febris rheumatica, glomerulo nephritis, Goodpasture's syndrome, Graves' disease, Harnman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoriasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antibodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as *Leishmania*, and immunosuppressed disease states such as viral infections following allograft transplantations, AIDS, cancer, chronic active hepatitis diabetes, toxic shock syndrome and food poisoning.

Furthermore, the invention relates to a method of treatment or prevention of diseases which comprises the administration of an effective amount of compounds of the formula (I) or a pharmaceutically acceptable salt or physiologically functional derivative or a stereoisomer thereof.

In a preferred embodiment, the invention relates to the use of compounds of the formula (I) or a pharmaceutically acceptable salt or physiologically functional derivative or a stereoisomer thereof if desired with appropriate adjuvants and additives for the production of a medicament for the treatment or prevention of skin diseases in which T cells play a role; especially preferably the skin diseases are selected from the group consisting of psoriasis, atopic dermatitis, alopecia areata, alopecia totalis, alopecia subtotalis, alopecia universalis, alopecia diffusa, lupus erythematodes of the skin, lichen planus, dermatomyostis of the skin, atopic eczema, morphea, sklerodermia, psoriasis vulgaris, psoriasis capitis, psoriasis guttata, psoriasis inversa, alopecia areata ophiasistype, androgenetic alopecia, allergic contact eczema, irritative contact eczema, contact eczema, pemphigus vulgaris, pemphigus foliaceus, pemphigus vegetans, scarring mucosal pemphigoid, bullous pemphgoid, mucous pemphigoid, dermatitis, dermatitis herpetiformis duhring, urticaria, necrobiosis lipoidica, erythema nodosum, lichen vidal, prurigo simplex, prurigo nodularis, prurigo acuta, linear IgA dermatosis, polymorphic light dermatoses, erythema solaris, lichen sclerosus et atrophicans, exanthema of the skin, drug exanthema, purpura chronica progressiva, dihidrotic eczema, Eczema, fixed drug exanthema, photoallergic skin reaction, lichen simplex eriorale, dermatitis and "Graft versus Host-Disease", acne, rosacea, scarring, keloids and vitiligo.

Moreover, the compounds of the present invention can be used for the treatment of diseases resulting from ischemia and/or reperfusion injury of organs and/or of parts of the body selected from the group comprising heart, brain, peripheral limb, kidney, liver, spleen and lung, and/or wherein the endothelial dysfunction is associated with diseases selected from a group comprising infarctions such as myocardial infarction and critical limb ischemia, and/or wherein the endothelial dysfunction is associated with diseases selected from the group comprising ischemic diseases such as peripheral arterial occlusive disease, e.g. critical leg ischemia, myocardial infarction and ischemic diseases of organs, e.g. of the kidney, spleen, brain and lung.

The compounds of this invention also can be applied for the prevention and the treatment of neurological diseases or disorders (diseases or disorders associated with the brain and nervous system), including but not limited to, Alzheimer's disease, Parkinson's disease, Creutzfeld-Jacob Disease, Lewy Body Dementia, amyotrophic lateral sclerosis, stroke, epilepsy, multiple sclerosis, myasthenia gravis, Huntington's Disease, Down's Syndrome, nerve deafness, and Meniere's disease.). Other neurological diseases and disorders will be apparent to those of skill in the art and are encompassed by the definition as used in this invention.

The compounds of the present invention can further be used for diseases that are caused by protozoal infestations in humans and animals. Such veterinary and human pathogenic protozoas are preferably intracellular active parasites of the phylum Apicomplexa or Sarcomastigophora, especially *Trypanosoma, Plasmodia, Leishmania, Babesia* and *Theileria, Cryptosporidia, Sacrocystida, Amoebia, Coccidia* and *Trichomonadia*. These active substances or corresponding drugs are especially suitable for the treatment of Malaria tropica, caused by *Plasmodium falciparum*, Malaria tertiana, caused by *Plasmodium vivax* or *Plasmodium ovale* and for the treatment of Malaria quartana, caused by *Plasmodium malariae*. They are also suitable for the treatment of Toxoplasmosis, caused by *Toxoplasma gondii*, Coccidiosis, caused for instance by *Isospora belli*, intestinal Sarcosporidiosis, caused by *Sarcocystis suihominis*, dysentery caused by *Entamoeba histolytica*, Cryptosporidiosis, caused by *Cryptosporidium parvum*, Chargas' disease, caused by *Trypanosoma cruzi*, sleeping sickness, caused by *Trypanosoma brucei rhodesiense* or *gambiense*, the cutaneous and visceral as well as other forms of Leishmaniosis. They are also suitable for the treatment of animals infected by veterinary pathogenic protozoa, like *Theileria parva*, the pathogen causing bovine East coast fever, *Trypanosoma congolense congolense* or *Trypanosoma vivax vivax*, *Trypanosoma brucei brucei*, pathogens causing Nagana cattle disease in Africa, *Trypanosoma brucei evansi* causing Surra, *Babesia bigemina*, the pathogen causing Texas fever in cattle and buffaloes, *Babesia bovis*, the pathogen causing European bovine Babesiosis as well as Babesiosis in dogs, cats and sheep, *Sarcocystis ovicanis* and *ovifelis* pathogens causing Sarcocystiosis in sheep, cattle and pigs, Cryptosporidia, pathogens causing Cryptosporidioses in cattle and birds, *Eimeria* and *Isospora* species, pathogens causing Coccidiosis in rabbits, cattle, sheep, goats, pigs and birds, especially in chickens and turkeys. The use of the compounds of the present invention is preferred in particular for the treatment of Coccidiosis or Malaria infections, or for the preparation of a drug or feed stuff for the treatment of these diseases. This treatment can be prophylactic or curative. In the treatment of malaria, the compounds of the present invention may be combined with other anti-malaria agents.

The compounds of the present invention can further be used for the prophylaxis and/or treatment of infectious diseases caused among others by bacteria and viruses, including opportunistic infections in a mammal, including a human. Said method comprises administering to the mammal an amount of at least one compound of the general formula (I) and/or pharmaceutically acceptable salts thereof, effective to prevent and/or treat said infectious disease and/or opportunistic infection.

The infectious disease can be selected from the group comprising AIDS, Alveolar Hydatid Disease (AHD, Echinococcosis), Amebiasis (*Entamoeba histolytica* Infection), Angiostrongylus Infection, Anisakiasis, Anthrax, Babesiosis (Babesia Infection), *Balantidium* Infection (Balantidiasis), *Baylisascaris* Infection (Raccoon Roundworm), Bilharzia (Schistosomiasis), *Blastocystis hominis* Infection (Blastomycosis), Boreliosis, Botulism, Brainerd Diarrhea, Brucellosis, BSE (Bovine Spongiform Encephalopathy), Candidiasis, Capillariasis (Capillaria Infection), CFS (Chronic Fatigue Syndrome), Chagas Disease (American Trypanosomiasis), Chickenpox (Varicella-Zoster virus), *Chlamydia pneumoniae* Infection, Cholera, Chronic Fatigue Syndrome, CJD (Creutzfeldt-Jakob Disease), Clonorchiasis (Clonorchis Infection), CLM (Cutaneous Larva Migrans, Hookworm Infection), Coccidioidomycosis, Conjunctivitis, Coxsackievirus A16 (Hand, Foot and Mouth Disease), Cryptococcosis, *Cryptosporidium* Infection (Cryptosporidiosis), *Culex* mosquito (Vector of West Nile Virus), Cutaneous Larva Migrans (CLM), Cyclosporiasis (Cyclospora Infection), Cysticercosis (Neurocysticercosis), Cytomegalovirus Infection (CMV), Dengue/Dengue Fever, *Dipylidium* Infection (Dog and Cat Flea Tapeworm), Ebola Virus Hemorrhagic Fever, Echinococcosis (Alveolar Hydatid Disease), Encephalitis, *Entomoeba coli* Infection, *Entomoeba dispar* Infection, *Entomoeba hartmanni* Infection, *Entomoeba histolytica* Infection (Amebiasis), *Entomoeba polecki* Infection, Enterobiasis (Pinworm Infection), Enterovirus Infection (Non-Polio), Epstein-Barr Virus Infection, *Escherichia coli* Infection, Foodborne Infection, Foot and mouth Disease, Fungal Dermatitis, Gastroenteritis, Group A streptococcal Disease, Group B streptococcal Disease, diseases caused by staphylococcal infections (*Staphylococcus aureus* and other *staphylococcus* species), diseases caused by infections with *pseudomonas aeruginosa* and other *pseudomonas* species, *Burkholderia cepacia* infections, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis, Herpes Zoster (Shingles), HIV Infection, Human Ehrlichiosis, Human Parainfluenza Virus Infection, Influenza, Isosporiasis (*Isospora* Infection), Lassa Fever, Leishmaniasis, Kala-azar (Kala-azar, *Leishmania* Infection), Leprosy, Lice (Body lice, Head lice, Pubic lice), Lyme Disease, Marburg Hemorrhagic Fever, Measles, Meningitis, Mosquito-borne Diseases, *Mycobacterium avium* Complex (MAC) Infection, *Naegleria* Infection, Nosocomial Infections, Nonpathogenic Intestinal Amebae Infection, Onchocerciasis (River Blindness), Opisthorciasis (Opisthorcis Infection), Parvovirus Infection, Plague, PCP (*Pneumocystis carinii* Pneumonia), Polio, Q Fever, Rabies, Respiratory Syncytial Virus (RSV) Infection, Rheumatic Fever, Rift Valley Fever, River Blindness (Onchocerciasis), Rotavirus Infection, Roundworms Infection, Salmonellosis, *Salmonella Enteritidis*, Scabies, Shigellosis, Shingles, Sleeping Sickness, Smallpox, Streptococcal Infection, Tapeworm Infection (*Taenia* Infection), Tetanus, Toxic Shock Syndrome, Tuberculosis, Ulcers (Peptic Ulcer Disease), Valley Fever, *Vibrio parahaemolyticus* Infection, *Vibrio vulnificus* Infection, Viral Hemorrhagic Fever, Warts, Waterborne infectious Diseases, West Nile Virus Infection (West Nile Encephalitis), Whooping Cough, Yellow Fever.

The compounds of formula (I), (II) or (III) and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of the formula (I), (II) or (III) or a salt thereof, in addition to customary pharmaceutically innocuous excipients and additives. The compounds of formula (I), (II) or (III) can also be administered in form of their salts, which are obtainable by reacting the respective compounds with physiologically acceptable acids and bases.

The production of medicaments containing the compounds of formula (I), (II) or (III) according to the invention and their application can be performed according to well-known pharmaceutical methods.

While the compounds of formula (I), (II) or (III) according to the invention for use in therapy may be administered in the form of the raw chemical compound, it is preferred to introduce the active ingredient, optionally in the form of a physiologically acceptable salt in a pharmaceutical composition together with one or more adjuvants, excipients, carriers, buffers, diluents, and/or other customary pharmaceutical auxiliaries. Such salts of the compounds may be anhydrous or solvated.

In a preferred embodiment, the invention provides medicaments comprising compounds of formula (I), (II) or (III) according to the invention, or a pharmaceutically acceptable salt or physiologically functional derivative or a stereoisomer thereof, together with one or more pharmaceutically acceptable carriers thereof, and, optionally, other therapeutic and/or prophylactic ingredients. The carrier(s) must be "acceptable" in the sense of being compatible with the other ingredients of the formulation and not harmful to the recipient thereof.

A medicament of the invention may be those suitable for oral, rectal, bronchial, nasal, topical, buccal, sub-lingual, transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The compounds according to the invention, together with a conventional adjuvant, carrier, or diluent, may thus be placed into the form of medicament and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such Medicament and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The compound useable according to the invention can be administered in a wide variety of oral and parenteral dosage forms. It will be obvious to those skilled in the art that the following dosage forms may comprise, as the active component, either a compound of formula (I), (II) or (III) according to the invention or a pharmaceutically acceptable salt or stereosomer thereof.

For preparing a medicament from a compounds of formula (I), (II), or (III) pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify. Compositions suitable for vaginal administration may be presented as pessaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds of formula (I), (II), or (III) according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilizing agents, and the like.

In one embodiment of the present invention, the medicament is applied topically or systemically or via a combination of the two routes.

In an especially preferred embodiment of the present invention the medicament is applied topically. This reduces possible side effects and limits the necessary treatment to those areas affected.

Preferably the medicament is prepared in form of an ointment, a gel, a plaster, an emulsion, a lotion, a foam, a cream of a mixed phase or amphiphilic emulsion system (oil/water-water/oil mixed phase), a liposome, a transfersome, a paste or a powder.

Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. Tablets or capsules for oral administration and liquids for intravenous administration and continuous infusion are preferred compositions.

Further details on techniques for formulation and administration may be found in the latest edition of Remington's Pharmaceutical Sciences (Maack Publishing Co. Easton, Pa.).

Pharmaceutical compositions can also contain two or more compounds of the formula (I), (II) or (III) or their pharmacologically acceptable salts and also other therapeutically active substances.

Thus, the compounds of the present invention can be used in the form of one compound alone or in combination with other active compounds—for example with medicaments already known for the treatment of the aforementioned diseases, whereby in the latter case a favorable additive, amplifying effect is noticed. Suitable amounts to be administered to humans may range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. In general, suitable dosage rates for larger mammals, for example humans, may be of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration. In the case of other administration forms too, the daily dose is in similar ranges. For topical delivery, depending on the permeability of the skin, the type and the severity of the disease and dependent on the type of formulation and frequency of application, different concentrations of active compounds within the medicament can be sufficient to elicit a therapeutic effect by topical application. Preferably the concentration of an active compound or a pharmaceutically acceptable salt thereof or a physiologically functional derivative or a stereoisomer thereof within a medicament according to the invention is in the range of between 1 µmol/l and 100 mmol/l.

The following examples and figures are included to demonstrate preferred embodiments of the invention. It should be appreciated by those of skill in the art that the techniques disclosed in the examples that follow represent techniques discovered by the inventors to function well in the practice of the invention, and thus can be considered preferred modes for its practice. However, those of skill in the art should, in light of the present disclosure, appreciate that many changes can be made in the specific embodiments that are disclosed without departing from the spirit and scope of the invention as set out in the appended claims. All references cited are incorporated herein by reference.

EXAMPLES

Abbreviations: min, minute(s); h, hour(s); r.t., room temperature; t-, tert-.

NMR spectra: Bruker Avance 300 MHz. The spectra were recorded at 300 MHz ($^1$H-NMR), respectively, using the residual solvent peak as an internal standard (DMSO-$d_6$, $\delta_H$=2.49; CD$_3$OD, $\delta_H$=3.31; CDCl$_3$, $\delta_H$=7.26; CD$_3$CN, $\delta_H$=1.93; (CD$_3$)$_2$CO, $\delta_H$=2.05).

Analytical LC/ESI-MS: 2× Waters 600 Multisolvent Delivery System. 50 µl sample loop. Column, Chromolith Speed ROD RP18e (Merck, Darmstadt), 50×4.6 mm, with 2 µm prefilter (Merck). Eluent A, H$_2$O+0.1% HCO$_2$H; eluent B, MeCN. Gradient, 5% B to 100% B within 5 min; flow, 3 ml/min. Waters LCZ single quadrupol mass spectrometer with electrospray source. MS method, MS8minPM-80-800-20V; positive/negative ion mode scanning, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

Preparative HPLC-MS: Waters 600 Multisolvent Delivery System with peparative pump heads. 2000 µl or 5000 µl sample loop. Column, Waters X-Terra RP18, 7 µm, 19×150 mm with X-Terra RP18 guard cartridge 7 µm, 19×10 mm; used at flow rate 20 ml/min or YMC ODS-A, 120 Å, 40×150 mm with X-Terra RP18 guard cartridge 7 µm, 19×10 mm; used at flow rate 50 ml/min. Make-up solvent: MeCN—H$_2$O—HCO$_2$H 80:20:0.05 (v:v:v). Eluent A, H$_2$O+0.1% HCO$_2$H; eluent B, MeCN. Different linear gradients from 5-100% eluent B, adapted to sample. Injection volume: 500 µl-2000 µl depending on sample. Waters ZQ single quadrupol mass spectrometer with electrospray source. Positive or negative ion mode scanning m/z 80-800 in 1 s; capillary, 3.5 kV or 3.0 kV; cone voltage, 20 V; multiplier voltage, 400 V; probe and desolvation gas temperature, 120° C. and 350° C., respectively. Waters Fraction Collector II with mass-triggered fraction collection. Waters 996 photo diode array detector.

Synthesis of 4-(Methoxy-methyl-carbamoyl)-piperidine-1-carboxylic acid t-butyl ester Piperidine-1,4-dicarboxylic acid mono-tert-butyl ester (1.0 eq, 21.8 mmol) was dissolved under inert conditions in 35 ml dry N,N-dimethylformamide. O,N-dimethyl-hydroxylamine hydrochloride (1.03 eq, 22.5 mmol), benzotriazol-1-ol monohydrate (1.03 eq, 22.5 mmol) and triethylamine (1.5 eq, 32.7 mmol) were added. The reaction mixture was cooled to 0° C., N-(3-Dimethylaminopropyl)-N-ethylcarbodiimid hydrochloride (1.0 eq, 21.8 mmol) was added over a period of 10 minutes and the mixture was stirred vigorously at 0° C. for 1 h and at r.t. for 18 h.

The solvent was removed under vacuum and the residue was suspended in 400 ml ethylacetate. The organic layer was extracted 3 times with 100 ml of 1 M citric acid, aqueous sodium carbonate and twice with 100 ml brine, dried over $MgSO_4$ and filtered. The solvent was removed and the residue was purified by distillation resulting in a yield of 80%.

Synthesis of 4-Formyl-piperidine-1-carboxylic acid t-butyl ester 4-(methoxy-methyl-carbamoyl)-piperidine-1-carboxylic acid tert-butyl ester (1.0 eq, 16.4 mmol) was dissolved in 100 ml dry tetrahydrofurane under inert atmosphere. This solution was added dropwise over a period of 1 h to a suspension of lithiumalanate (3.0 eq, 49.6 mmol) in 70 ml dry tetrahydrofurane at −50° C. During the adding of the mixture, the temperature was held at −50° C. and then allowed to warm to 0° C. within 3 h. The mixture was cooled to −78° C. and quenched carefully with 100 ml 1 M citric acid. The mixture was warmed up to r.t. and diluted with 400 ml ethylacetate. The phases were separated and the aqueous phase was extracted 3 times with 70 ml ethylacetate. The combined organic layers were extracted 3 times with 100 ml 1 M citric acid, aqueous sodium carbonate and 2 times with 100 ml brine, dried over $MgSO_4$ and filtrated. The solvent was removed and the residue was purified by distillation resulting in a yield of 85%

Synthesis of 4-(4-Ethoxycarbonyl-4,5-dihydro-thiazol-2-yl)-piperidine-1-carboxylic acid t-butyl ester 4-formyl-piperidine-1-carboxylic acid tert-butyl ester (1.0 eq, 13 mmol) was dissolved under inert conditions in 40 ml toluene. To this solution L-cystein ethylester hydrochloride (1.6 eq, 21 mmol) and triethylamine (1.6 eq, 21 mmol) were added. The mixture was refluxed for 14 h. The generated water was removed with a Dean & Stark trap.

The solvent was removed and the residue was dissolved in 100 ml ethylacetate. The organic layer was extracted 3 times with 50 ml 1 M citric acid, aqueous potassium hydrogen carbonate and 2 times with 50 ml brine, dried over $MgSO_4$ and filtrated. The solvent was removed and the residue was purified by silica gel chromatography using a PE/EA 4:1 gradient. Yield: 75%

Synthesis of 4-(4-Ethoxycarbonyl-thiazol-2-yl)-piperidine-1-carboxylic acid t-butyl ester 4-(4-Ethoxycarbonyl-4,5-dihydro-thiazol-2-yl)-piperidine-1-carboxylic acid tert-butyl ester (1.0 eq, 8.7 mmol) was solved in 160 ml toluene under inert conditions. To this solution $MnO_2$ (15.0 eq, 130 mmol) was added. The reaction was heated to 70° C. under stirring for 5 h. The mixture was filtered over celite and the filtration agent was washed 3 times with 30 ml toluene and ethylacetate. The combined organic layers were distilled in vacuo. The residue was purified by silica gel chromatography using a DCM/MeOH 95:5 gradient. Yield: 30%

C-Terminal Functionalisation 4-(4-Ethoxycarbonyl-thiazol-2-yl)-piperidine-1-carboxylic acid tert-butyl ester (1.0 eq, 2.9 mmol) was dissolved under inert gas in 40 ml dioxane. Under stirring 1.5 ml aqueous 2 N NaOH was added dropwise over a period of 10 min. Afterwards the mixture was stirred for 2 h at r.t.

The reaction was neutralized with 2 N HCl and the solvent was evaporated in vacuo. The residue was dissolved in 50 ml ethylacetate. The organic layer was extracted 3 times with 10 ml of 1 M citric acid and water, dried over $MgSO_4$ and filtered. The solvent was removed and the residue was dried in vacuo. Yield 95%

4-(4-Carboxy-thiazol-2-yl)-piperidine-1-carboxylic acid tert-butyl ester (1 eq) was dissolved under inert conditions in dry dimethylacetamide (0.03 mmol/ml). To this solution aryl- or alkylamine (1 eq), diisopropylethylamine (2 eq) and O-benzotriazol-1-yl-N,N,N',N'-tetramethyluronium hexafluorophosphate (2 eq) was added. The reaction mixture was stirred for 12 h at r.t.

The solvent was removed in vacuo and the residue was dissolved in ethylacetate. The organic layer was extracted 3 times with 1 M citric acid, aqueous potassium hydrogen carbonate and 2 times with brine, dried over $MgSO_4$ and filtered. The solvent was removed and the residue was purified by silica gel chromatography using a DCM/MeOH 95:5 gradient. Yield: 40-80%

N-Terminal Functionalisation

The N-protected substrate was treated under inert condition with 4 M HCl/dioxane (conc. 0.03 mmol substrate in 1 mL HCl/dioxane) and was stirred for 2 h at r.t.

The solvent was removed in vacuo to yield the HCl salt of the free amine without further purification.

The free amino compound (1 eq) was dissolved under inert conditions in dry dimethylacetamide (0.03 mmol/ml). To this solution aryl- or alkylcarboxylic acid (1 eq), diisopropylethylamine (2 eq) and O-benzotriazol-1-yl-N,N,N',N'-tetramethyluronium hexafluorophosphate (2 eq) was added in this sequence and the reaction mixture was stirred for 12 h at r.t.

The solvent was removed in vacuo and the residue was dissolved in ethylacetate. The organic layer was extracted 3 times with 1 M citric acid, aqueous potassium hydrogen carbonate and 2 times with brine, dried over $MgSO_4$ and filtered. The solvent was removed and the residue was purified by silica gel chromatography using a DCM/MeOH 95:5 gradient. Yield: 40-80%

General Synthesis for Compounds of Type (III) and (II)

Procedure for the Synthesis of Compounds of Type (IIIa), (IIIc), (IIa) and (IIb)

$7.3 \times 10^{-4}$ mol of the benzoic acid derivative (VI) was dissolved in 5 ml DMF and 1 eq. of Hünig's base was added, stirring the reaction mixture for a few minutes, followed by the addition of 1 eq. of HBTU and further stirring at r.t. for 2 min. Afterwards 1 eq. 2-Amino-thiazole-4-carboxylic acid ethyl ester was added, stirring the mixture overnight at the same temperature. Subsequently, the solvent was removed by filtration and the residue redissolved in 5 ml dioxane and treated with 0.5 ml of a 1M NaOH solution. After the reaction was complete, the pH was decreased to 1-2 with a 1M HCl solution and the precipitated product (VII) filtered and dried in vacuo. For the next step, intermediate (VII) was dissolved in 3 ml DMF and 1 eq. of Hünig's base was added, stirring the reaction mixture for a few minutes, followed by the addition of 1 eq. of HBTU and further stirring at r.t. for 2 min. Afterwards 1 eq. the amino component was added, stirring the mixture overnight at the same temperature. Subsequently, the solvent was removed by filtration and the crude product redissolved in 10 ml ethyl acetate, washed twice with 10 ml citric acid (1M solution), 10 ml sat. NaHCO$_3$ solution and 10 ml water. The organic phase was then evaporated and the residue dried over MgSO$_4$. The solvent was removed and final purification was realised by preparative HPLC as described above.

As a second variant for the first step, the corresponding acid chloride derivative of (VI) could be reacted with the 2-Amino-thiazole-4-carboxylic acid ethyl ester (1:1) using 1.1 eq. of Hünig's base.

Procedure for the Synthesis of Compounds of Type (IIIb, d, e, f) and (IIc, d)

$6.3 \times 10^{-4}$ mol of 2-Bromo-thiazole-4-carboxylic acid ethyl ester (X) was dissolved in 10 ml THF together with 2.2 eq. of the respective piperazine (IX), allowing to reflux overnight. Afterwards the solvent was removed in vacuo and the residue purified by pTLC (PE/EE 2/1).

The second and the third step of the reaction were accomplished as described above under the procedure for the synthesis of compounds of type (IIIa) and (IIIc).

For as synthesis-protocol of type (IIIb, d, e, f and IIc, d) compounds with Z═CH, see WO 2004/058750.

Exemplary compounds of formula (I) of the present invention include, but are not limited to, the followings:

| Cp. | Name | Mass | LC/(+)-ESI-MS: | $^1$H-NMR |
|---|---|---|---|---|
| 1 | [4-(1H-Indol-3-yl)-piperidin-1-yl]-{2-[1-(pyrazine-2-carbonyl)-piperidin-4-yl]-thiazol-4-yl}-methanone | 501 | 502 [M + H]$^+$ | δ = 1.69-2.04 (m, 4H, 2 CH$_2$), 2.07-2.24 (m, 4H, 2 CH$_2$), 2.96-3.4 (m, 6H, 2 CH$_2$, 2 CH), 4.05-4.91 (m, 4H, 2 CH$_2$), 6.99-7.78 (m, 6H, CH$_{Ar}$), 8.01 (s, 1H, NH), 8.5-8.9 (m, 3H, CH$_{Ar}$). |
| 2 | 4-[5-(4-{4-[4-(1H-Indol-3-yl)-piperidine-1-carbonyl]-thiazol-2-yl}-piperidin-1-yl)-5-oxo-pentyl]-tetrahydro-thieno[3,4-d]imidazol-2-one | 621 | 622 [M + H]$^+$ | |
| 3 | 4-[4-(4-Benzhydryl-piperazine-1-carbonyl)-thiazol-2-yl]-piperidine-1-carboxylic acid tert-butyl ester | 547 | 548 [M + H]$^+$ | |
| 4 | 2-Phenyl-1-(4-{4-[4-(3-trifluoromethyl-phenyl)-piperazine-1-carbonyl]-thiazol-2-yl}-piperidin-1-yl)-ethanone | 543 | 544 [M + H]$^+$ | δ = 1.48-1.69 (m, 2H, CH$_2$), 2.02-2.13 (m, 2H, CH$_2$), 2.70-2.9 (m, 2H, CH$_2$), 3.22-3.38 (m, 5H, 2 CH$_2$), 1 CH), 3.74 (s, 2H, CH$_2$), 4.51-4.60 (m, 2H, 1 CH$_2$), 7.06-7.91 (m, 10H CH$_{Ar}$). |
| 5 | 3-[2-(4-{4-[4-(1H-Indol-3-yl)-piperidine-1-carbonyl]-thiazol-2-yl}-piperidin-1-yl)-2-oxo-ethyl]-5-methoxy-indan-1-one | 597 | 598 [M + H]$^+$ | |
| 6 | 2-(4-Fluoro-phenyl)-1-(4-{4-[4-(3-trifluoromethyl-phenyl)-piperazine-1-carbonyl]-thiazol-2-yl}-piperidin-1-yl)-ethanone | 561 | 562 [M + H]$^+$ | δ = 1.58-1.7 (m, 2H, CH$_2$), 2.06-2.18 (m, 2H, CH$_2$), 2.75 (s, 2H, CH$_2$) 2.78-2.9 (m, 2H, CH$_2$), 3.27-3.38 (m, 5H, 2 CH$_2$, 1 CH), 4.5-4.61 (m, 2H, CH$_2$), 7.02-7.94 (m, 9H CH$_{Ar}$). |
| 7 | 2,2-Diphenyl-1-(4-{4-[4-(3-trifluoromethyl-phenyl)-piperazine-1-carbonyl]-thiazol-2-yl}-piperidin-1-yl)-ethanone | 619 | 620 [M + H]$^+$ | δ = 1.3-1.75 (m, 2H, CH$_2$) 1.94-2.19 (m, 2H, CH$_2$), 2.9-3.02 (m, 2H, CH$_2$) 3.18-3.43 (m, 6H, 2 CH, 2 CH$_2$) 4.18-4.7 (m, 2H, CH$_2$), 7.11-7.95 (m, 15H, CH$_{Ar}$). |
| 8 | 1-(4-{4-[4-(1H-Indol-3-yl)-piperidine-1-carbonyl]-thiazol-2-yl}-piperidin-1-yl)-3,3-diphenyl-propan-1-one | 603 | 604 [M + H]$^+$ | |
| 9 | 4-{4-[4-(3-Trifluoromethyl-phenyl)-piperazine-1-carbonyl]-thiazol-2-yl}-piperidine-1-carboxylic acid tert-butyl ester | 525 | 526 [M + H]$^+$ | δ = 1.45 (s, 9H, 3 CH$_3$), 1.65-1.78 (m, 2H, CH$_2$), 2.05-2.18 (m, 2H, CH$_2$), 2.91-3.03 (m, 2H, CH$_2$), 3.29 (m$_c$, 1H, CH), 3.38 (m$_c$, 1H, 2 CH$_2$) 4.10-4.19 (m, 2H, CH$_2$), 7.10-7.96 (m, 5H, CH$_{Ar}$) |
| 10 | (2-Piperidin-4-yl-thiazol-4-yl)-[4-(3-trifluoromethyl-phenyl)-piperazin-1-yl]-methanone | 424 | 425 [M + H]$^+$ | |

-continued

| Cp. | Name | Mass | LC/(+)-ESI-MS: | ¹H-NMR |
|---|---|---|---|---|
| 11 | {2-[1-(4,7-Dimethyl-pyrazolo[5,1-c][1,2,4]triazine-3-carbonyl)-piperidin-4-yl]-thiazol-4-yl}-[4-(1H-indol-3-yl)-piperidin-1-yl]-methanone | 569 | 570 [M + H]⁺ | δ = 1.75-2.07 (m, 4H, 2 CH₂), 2.08-2.42 (m, 4H, 2 CH₂), 2.63 (s, 3H, CH₃), 2.87 (s, 3H, CH₃), 2.94-3.4 (m, 6H, 2 CH₂, 2 CH), 3.83 (m$_c$, 1H, CH₂), 4.44-4.6 (m, 1H, CH₂) 4.84 (m$_c$, 2H, CH₂), 6.98-7.79 (m, 7H, CH$_{Ar}$), 8.02 (s, 1H, NH). |
| 12 | 1-(4-{4-[4-(1H-Indol-3-yl)-piperidine-1-carbonyl]-thiazol-2-yl}-piperidin-1-yl)-2-phenyl-ethanone | 513 | 514 [M + H]⁺ | δ = 1.65-1.93 (m, 4H, 2 CH₂), 1.96-2.24 (m, 4H, 2 CH₂), 2.77-2.91 (m, 2H, CH₂), 2.93-3.05 (m, 1H, CH₂), 3.07-3.2 (m, 2H, 2 CH) 3.25-3.34 (m, 1H, CH₂), 3.76 (s, 2H, CH₂), 3.94 (m$_c$, 1H, CH₂), 4.43-4.57 (m, 1H, CH₂), 4.66 (m$_c$, 1H, CH₂), 4.75-4.90 (m, 1H, CH₂), 6.98-7.75 (m, 11H, CH$_{Ar}$), 7.98 (s, 1H, NH). |
| 13 | 5-Methoxy-3-[2-oxo-2-(4-{4-[4-(3-trifluoromethyl-phenyl)-piperazine-1-carbonyl]-thiazol-2-yl}-piperidin-1-yl)-ethyl]-indan-1-one | 627 | 628 [M + H]⁺ | |
| 14 | 1-(4-Fluoro-phenyl)-2-(4-{4-[4-(1H-indol-3-yl)-piperidine-1-carbonyl]-thiazol-2-yl}-piperidin-1-yl)-ethanone | 531 | 532 [M + H]⁺ | δ = 1.58-1.85 (m, 4H, 2 CH₂), 2.07-2.19 (m, 4H, 2 CH₂), 2.64-3.64 (m, 6H, 2 CH₂, 2 CH), 3.97 (m$_c$, 1H, CH₂), 4.41 (m$_c$, 2H, CH₂) 4.49-4.7 (m, 1H, CH₂) 5.48 (s, 2H, CH₂), 6.84-7.71 (m, 10H CH$_{Ar}$). |
| 15 | 3-Phenyl-1-(4-{4-[4-(3-trifluoromethyl-phenyl)-piperazine-1-carbonyl]-thiazol-2-yl}-piperidin-1-yl)-propynone | 553 | 554 [M + H]⁺ | δ = 1.71-1.97 (m 2H, CH₂), 2.20-2.35 (m, 2H, CH₂), 3.02 (m$_c$, 1H, CH) 3.42-3.55 (m, 6H, 2 CH₂), 4.51-4.61 (m, 2H, CH₂), 7.2-8.0 (m, 9H, CH$_{Ar}$). |
| 16 | 3,3-Diphenyl-1-(4-{4-[4-(3-trifluoromethyl-phenyl)-piperazine-1-carbonyl]-thiazol-2-yl}-piperidin-1-yl)-propan-1-one | 633 | 634 [M + H]⁺ | δ = 1.44-1.59 (m, 2H, CH₂) 2.04-2.12 (m, 2H, CH₂), 2.7-2.83 (m, 2H, CH₂), 3.08-3.34 (m, 4H, 2 CH, CH₂), 3.34-3.41 (m, 4H, 2 CH₂), 4.46-463 (m, 2H, CH₂), 7.11-7.95 (m, 15H, CH$_{Ar}$). |
| 17 | {2-[1-(Pyrazine-2-carbonyl)-piperidin-4-yl]-thiazol-4-yl}-[4-(3-trifluoromethyl-phenyl)-piperazin-1-yl]-methanone | 531 | 532 [M + H]⁺ | δ = 1.83-1.99 (m, 2H, CH₂), 2.07-2.35 (m, 2H, CH₂), 2.73-2.95 (m, 2H, CH₂), 3.13 (m$_c$, 1H, CH), 3.33-3.44 (m, 4H, 2 CH₂), 4.6-4.74 (m, 2H, CH₂), 7.11-8.88 (m, 8H, CH$_{Ar}$). |
| 18 | {2-[1-(4,7-Dimethyl-pyrazolo[5,1-c][1,2,4]triazine-3-carbonyl)-piperidin-4-yl]-thiazol-4-yl}-[4-(3-trifluoromethyl-phenyl)-piperazin-1-yl]-methanone | 599 | 600 [M + H]⁺ | |
| 19 | 4-(4-{2-[4-(1H-Indol-3-yl)-piperidin-1-carbonyl]}-thiazol-2-yl)-piperidine-1-carboxylic acid tert-butyl ester | 495 | 496 [M + H]⁺ | δ = 1.46 (s 9H 3 CH₃), 1.67-1.92 (m, 4H, 2 CH₂), 2.06-2.23 (m, 4H, 2 CH₂), 2.84-2.95 (m, 2H, 1 CH₂), 2.97-3.08 (m, 1H, 1 CH₂), 3.1-3.22 (m, 2H, 2CH) 3.23-3.36 (m, 1H, 1 CH₂), 4.11-4.23 (m, 2H, 1 CH₂), 4.5-4.91 (m, 2H 1 CH₂), 6.96-7.77 (m, 6H CH$_{Ar}$), 7.98 (s 1H, NH). |
| 20 | 1-{4-[4-(4-Benzhydryl-piperazine-1-carbonyl)-thiazol-2-yl]-piperidin-1-yl}-2-(4-fluoro-phenyl)-ethanone | 583 | 584 [M + H]⁺ | |
| 21 | (4-Benzhydryl-piperazin-1-yl)-{2-[1-(4,7-dimethyl-pyrazolo[5,1-c][1,2,4]triazine-3-carbonyl)-piperidin-4-yl]-thiazol-4-yl}-methanone | 621 | 622 [M + H]⁺ | |
| 22 | (4-Benzhydryl-piperazin-1-yl)-(2-piperidin-4-yl-thiazol-4-yl)-methanone | 447 | 448 [M + H]⁺ | |

-continued

| Cp. | Name | Mass | LC/(+)-ESI-MS: | ¹H-NMR |
|---|---|---|---|---|
| 23 | 1-{4-[4-(4-Benzhydryl-piperazine-1-carbonyl)-thiazol-2-yl]-piperidin-1-yl}-2-phenyl-ethanone | 565 | 566 [M + H]⁺ | δ = 1.35 (m$_C$, 1H, CH$_2$), 1.60 (m$_C$, 1H, CH$_2$), 1.93 (m$_C$, 2H, CH$_2$), 2.37 (m$_C$, 4H, 2 CH$_2$), 2.71 (m$_C$, 1H, CH$_2$), 2.97-3.12 (m, 2H, CH$_2$, CH), 3.67 (s, 2H, CH$_2$), 3.69-3.91 (m, 5H, 6 CH$_2$), 4.18 (s, 1H, CH), 4.58 (m$_C$, 1H, CH$_2$), 7.09-7.68 (m, 16H, CH$_{Ar}$). |
| 24 | 3-(2-{4-[4-(4-Benzhydryl-piperazine-1-carbonyl)-thiazol-2-yl]-piperidin-1-yl}-2-oxo-ethyl)-5-methoxy-indan-1-one | 649 | 650 [M + H]⁺ | |

Exemplary compounds of formula (I), (II) and (III) of the present invention include, but are not limited to, the followings:

| Cp. | Name | Mass | LC/(+)-ESI-MS: | Biological activity[1] |
|---|---|---|---|---|
| 1 | 2-Morpholin-4-yl-thiazole-4-carboxylic acid (5,6-dimethyl-1H-benzoimidazol-2-yl)-amide | 357 | 358 [M + H]⁺ | + |
| 2 | 2-[3-(2-Trifluoromethoxy-phenyl)-ureido]-thiazole-4-carboxylic acid (1H-benzoimidazol-2-yl)-amide | 462 | 463 [M + H]⁺ | + |
| 3 | N-{4-[4-(4-Fluoro-phenyl)-piperazine-1-carbonyl]-thiazol-2-yl}-2-trifluoromethoxy-benzamide | 494 | 495 [M + H]⁺ | ++ |
| 4 | 2-(2-Fluoro-benzoylamino)-thiazole-4-carboxylic acid (5,6-dimethyl-1H-benzoimidazol-2-yl)-amide | 409 | 410 [M + H]⁺ | + |
| 5 | N-[5-(4-Pyrimidin-2-yl-piperazine-1-carbonyl)-thiazol-2-yl]-2-trifluoromethoxy-benzamide | 478 | 479 [M + H]⁺ | + |
| 6 | N-{4-[N'-(1H-Benzoimidazol-2-yl)-guanidinocarbonyl]-thiazol-2-yl}-3,4-difluoro-benzamide | 441 | 442 [M + H]⁺ | ++ |
| 7 | N-{4-[N'-(1H-Benzoimidazol-2-yl)-guanidinocarbonyl]-thiazol-2-yl}-4-fluoro-benzamide | 423 | 424 [M + H]⁺ | ++ |
| 8 | N-{4-[N'-(1H-Benzoimidazol-2-yl)-guanidinocarbonyl]-oxazol-2-yl}-2-trifluoromethoxy-benzamide | 473 | 474 [M + H]⁺ | +++ |
| 9 | 2-(2-Trifluoromethoxy-benzoylamino)-thiazole-4-carboxylic acid (4-dimethylamino-[1,3,5]triazin-2-yl)-amide | 453 | 454 [M + H]⁺ | + |
| 10 | N-{4-[N'-(1H-Benzoimidazol-2-yl)-guanidinocarbonyl]-thiazol-2-yl}-4-bromo-benzamide | 483 | 484 [M + H]⁺ | ++ |
| 11 | N-{4-[N'-(1H-Benzoimidazol-2-yl)-guanidinocarbonyl]-thiazol-2-yl}-2-methoxy-benzamide | 435 | 436 [M + H]⁺ | ++ |
| 12 | N-{4-[N'-(1H-Benzoimidazol-2-yl)-guanidinocarbonyl]-thiazol-2-yl}-2-trifluoromethoxy-benzamide | 489 | 490 [M + H]⁺ | +++ |
| 13 | N-(1H-Benzoimidazol-2-yl)-N'-{2-[4-(2-trifluoromethoxy-benzoyl)-piperazin-1-yl]-thiazole-4-carbonyl}-guanidine | 558 | 559 [M + H]⁺ | + |
| 14 | N-(1H-Benzoimidazol-2-yl)-N'-[2-(2,3-dihydro-benzo[1,4]dioxin-2-yl)-thiazole-4-carbonyl]-guanidine | 420 | 421 [M + H]⁺ | + |
| 15 | 2-Methoxy-N-{4-[4-(3-trifluoromethyl-phenyl)-piperazine-1-carbonyl]-thiazol-2-yl}-benzamide | 490 | 491 [M + H]⁺ | +++ |
| 16 | 3-Fluoro-4-trifluoromethyl-N-(1-{4-[4-(3-trifluoromethyl-phenyl)-piperazine-1-carbonyl]-thiazol-2-yl}piperidin-4-ylmethyl)-benzamide | 643 | 644 [M + H]⁺ | ++ |

-continued

| Cp. | Name | Mass | LC/(+)-ESI-MS: | Biological activity[1] |
|---|---|---|---|---|
| 17 | 3-Cyclopentyl-N-(1-{4-[4-(3-trifluoromethyl-phenyl)-piperazine-1-carbonyl]-thiazol-2-yl}-piperidin-4ylmethyl)-propionamide | 577 | 578 [M + H]+ | ++ |
| 18 | 2-Trifluoromethoxy-N-(1-{4-[4-(3-trifluoromethyl-phenyl)-piperazine-1-carbonyl]-thiazol-2-yl}-piperidin-4ylmethyl)-benzamide | 641 | 642 [M + H]+ | ++ |
| 19 | 4-Cyano-N-(1-{4-[4-(3-trifluoromethyl-phenyl)-piperazine-1-carbonyl]-thiazol-2-yl}-piperidin-4-ylmethyl)-benzamide | 582 | 583 [M + H]+ | ++ |
| 20 | [4-(3-Trifluoromethyl-phenyl)-piperazin-1-yl]-{2-[4-(4-trifluoromethyl-phenyl)-piperazin-1-yl]-thiazol-4-yl}-methanone | 569 | 570 [M + H]+ | ++ |
| 21 | {2-[4-(4-Trifluoromethoxy-phenyl)-piperazin-1-yl]-thiazol-4-yl}-[4-(3-trifluoromethyl-phenyl)-piperazin-1-yl]-methanone | 585 | 586 [M + H]+ | + |
| 22 | {2-[4-(2-Trifluoromethoxy-benzyl)-piperazin-1-yl]-thiazol-4-yl}-[4-(3-trifluoromethyl-phenyl)-piperazin-1-yl]-methanone | 599 | 600 [M + H]+ | +++ |
| 23 | {2-[4-(4-Bromo-benzyl)-piperazin-1-yl]-thiazol-4-yl}-[4-(3-trifluoromethyl-phenyl)-piperazin-1-yl]-methanone | 593 | 594 [M + H]+ | +++ |
| 24 | {2-[4-(3-Trifluoromethoxy-benzyl)-piperazin-1-yl]-thiazol-4-yl}-[4-(3-trifluoromethyl-phenyl)-piperazin-1-yl]-methanone | 599 | 600 [M + H]+ | +++ |
| 25 | 2-(2-Trifluoromethoxy-benzoylamino)-thiazole-4-carboxylic acid (5,6-dimethyl-1H-benzoimidazol-2-yl)-amide | 475 | 476 [M + H]+ | +++ |
| 26 | 2-(3-Fluoro-4-trifluoromethyl-benzoylamino)-oxazole-4-carboxylic acid ethyl ester | 536 | 537 [M + H]+ | +++ |
| 27 | N-{4-[N'-(1H-Benzoimidazol-2-yl)-guanidinocarbonyl]-oxazol-2-yl}-3-fluoro-4-trifluoromethyl-benzamide | 475 | 476 [M + H]+ | +++ |
| 28 | N-{4-[N'-(1H-Benzoimidazol-2-yl)-guanidinocarbonyl]-oxazol-2-yl}-2-trifluoromethoxy-benzamide | 473 | 474 [M + H]+ | +++ |
| 29 | {2-[1-(2,5-Dimethoxy-phenyl)-piperidin-4-yl]-thiazol-4-yl}-[4-(3-trifluoromethyl-phenyl)-piperazin-1-yl]-methanone | 560 | 561 | ++ |
| 30 | N-(1H-Benzoimidazol-2-yl)-N'-[2-(4-benzyl-piperazin-1-yl)-thiazole-4-carbonyl]-guanidine | 460 | 461 [M + H]+ | +++ |
| 31 | 2-(2-Trifluoromethoxy-benzoylamino)-thiazole-4-carboxylic acid (1H-benzoimidazol-2-yl)-amide | 447 | 448 [M + H]+ | +++ |
| 32 | 2-Trifluoromethoxy-N-{4-[4-(3-trifluoromethyl-phenyl)-piperazine-1-carbonyl]-thiazol-2-yl}-benzamide | 544 | 545 [M + H]+ | +++ |
| 33 | 3-Cyclopentyl-N-{4-[4-(3-trifluoromethyl-phenyl)-piperazine-1-carbonyl]-thiazol-2-yl}-propionamide | 480 | 481 [M + H]+ | +++ |
| 34 | 3-Fluoro-4-trifluoromethyl-N-{4-[4-(3-trifluoromethyl-phenyl)-piperazine-1-carbonyl]-thiazol-2-yl}-benzamide | 546 | 547 [M + H]+ | +++ |
| 35 | {2-[1-(3,3-Diphenyl-propyl)-piperidin-4-yl]-thiazol-4-yl}-[4-(3-trifluoromethyl-phenyl)-piperazin-1-yl]-methanone | 618 | 619 [M + H]+ | +++ |
| 36 | N-(1H-Benzoimidazol-2-yl)-N'-{2-[1-(2-trifluoromethoxy-benzoyl)-piperidin-4-yl]-thiazole-4-carbonyl}-guanidine | 557 | 558 [M + H]+ | +++ |
| 37 | 3-Cyclopentyl-1-(4-{4-[4-(3-trifluoromethyl-phenyl)-piperazine-1-carbonyl]-thiazol-2-yl}-piperazin-1-yl)-propan-1-one | 549 | 550 [M + H]+ | +++ |
| 38 | {2-[4-(2-Methoxy-benzoyl)-piperazin-1-yl]-thiazol-4-yl}-[4-(3-trifluoromethyl-phenyl)-piperazin-1-yl]-methanone | 559 | 560 [M + H]+ | +++ |
| 39 | {2-[4-(2-Trifluoromethoxy-benzoyl)-piperazin-1-yl]-thiazol-4-yl}-[4-(3-trifluoromethyl-phenyl)-piperazin-1-yl]-methanone | 613 | 614 [M + H]+ | +++ |

| Cp. | Name | Mass | LC/(+)-ESI-MS: | Biological activity[1] |
|---|---|---|---|---|
| 40 | 2-(2-Trifluoromethoxy-benzoylamino)-oxazole-4-carboxylic acid (5,6-dimethyl-1H-benzoimidazol-2-yl)-amide | 459 | 460 [M + H]+ | +++ |
| 41 | N-{4-[4-(3,4-Dichloro-phenyl)-piperazine-1-carbonyl]-thiazol-2-yl}-2-trifluoromethoxy-benzamide | 544 | 545 [M + H]+ | +++ |
| 42 | 2-(2-Trifluoromethoxy-benzoylamino)-thiazole-4-carboxylic acid [6-(4-methyl-piperazin-1-yl)-benzothiazol-2-yl]-amide | 562 | 563 [M + H]+ | +++ |
| 43 | 2-(2-Trifluoromethoxy-benzoylamino)-thiazole-4-carboxylic acid (5-nitro-1H-benzoimidazol-2-yl)-amide | 492 | 493 [M + H]+ | +++ |
| 44 | N-{4-[4-(2-Methoxy-phenyl)-piperazine-1-carbonyl]-thiazol-2-yl}-2-trifluoromethoxy-benzamide | 506 | 507 [M + H]+ | ++ |
| 45 | N-{4-[N'-(1H-Benzoimidazol-2-yl)-guanidinocarbonyl]-thiazol-2-yl}-2-cyclohexyl-benzamide | 487 | 488 [M + H]+ | +++ |
| 46 | 2-(2-Trifluoromethoxy-benzoylamino)-thiazole-4-carboxylic acid (1-methyl-1H-benzoimidazol-2-yl)-amide | 461 | 462 [M + H]+ | +++ |
| 47 | 2-(2-Trifluoromethoxy-benzoylamino)-thiazole-4-carboxylic acid [5-(propane-1-sulfonyl)-1H-benzoimidazol-2-yl]-amide | 553 | 554 [M + H]+ | +++ |
| 48 | {4-[1-(4-Fluoro-benzyl)-1H-benzoimidazol-2-yl]-piperazin-1-yl}-{2-[1-(2-trifluoromethoxy-benzoyl)-piperidin-4-yl]-thiazol-4-yl}-methanone | 692 | 693 [M + H]+ | +++ |
| 49 | N-(1H-Benzoimidazol-2-yl)-N'-(2-morpholin-4-yl-thiazole-4-carbonyl)-guanidine | 371 | 372 [M + H]+ | +++ |
| 50 | N-{5-[N'-(1H-Benzoimidazol-2-yl)-guanidinocarbonyl]-thiazol-2-yl}-2-trifluoromethoxy-benzamide | 489 | 490 [M + H]+ | +++ |
| 51 | N-{4-[N'-(1H-Benzoimidazol-2-yl)-guanidinocarbonyl]-thiazol-2-yl}-4-trifluoromethyl-benzamide | 473 | 474 [M + H]+ | +++ |
| 52 | 2-[1-(2-Trifluoromethoxy-benzoyl)-piperidin-4-yl]-thiazole-4-carboxylic acid [5-(propane-1-sulfonyl)-1H-benzoimidazol-2-yl]-amide | 621 | 622 [M + H]+ | +++ |
| 53 | N-{4-[N'-(1H-Benzoimidazol-2-yl)-guanidinocarbonyl]-thiazol-2-yl}-2-fluoro-4-trifluoromethyl-benzamide | 491 | 492 [M + H]+ | +++ |
| 54 | 1-{4-[N'-(1H-Benzoimidazol-2-yl)-guanidinocarbonyl]-thiazol-2-yl}-3-(2-trifluoromethoxy-phenyl)-urea | 504 | 505 [M + H]+ | +++ |
| 55 | 1-(2-Trifluoromethoxy-phenyl)-3-{4-[4-(3-trifluoromethyl-phenyl)-piperazine-1-carbonyl]-thiazol-2-yl}-urea | 559 | 560 [M + H]+ | +++ |
| 56 | N-{4-[N'-(1H-Benzoimidazol-2-yl)-guanidinocarbonyl]-thiazol-2-yl}-3-fluoro-4-trifluoromethyl-benzamide | 491 | 492 [M + H]+ | +++ |
| 57 | N-{4-[N'-(1H-Benzoimidazol-2-yl)-guanidinocarbonyl]-thiazol-2-yl}-2,6-difluoro-benzamide | 441 | 442 [M + H]+ | +++ |
| 58 | N-[4-(4-Benzhydryl-piperazine-1-carbonyl)-thiazol-2-yl]-2-trifluoromethoxy-benzamide | 566 | 567 [M + H]+ | ++ |
| 59 | {2-[4-(3,5-Bis-trifluoromethyl-benzoyl)-piperazin-1-yl]-thiazol-4-yl}-[4-(3-trifluoromethyl-phenyl)-piperazin-1-yl]-methanone | 665 | 666 [M + H]+ | + |
| 60 | {2-[4-(3-Fluoro-4-trifluoromethyl-benzoyl)-piperazin-1-yl]-thiazol-4-yl}-[4-(3-trifluoromethyl-phenyl)-piperazin-1-yl]-methanone | 615 | 616 [M + H]+ | +++ |
| 61 | 4-(4-{4-[4-(3-Trifluoromethyl-phenyl)-piperazine-1-carbonyl]-thiazol-2-yl}-piperazine-1-carbonyl)-benzonitrile | 554 | 555 [M + H]+ | +++ |
| 62 | 4-(4-{4-[4-(3-Trifluoromethyl-phenyl)-piperazine-1-carbonyl]-thiazol-2-yl}-piperazine-1-ylmethyl)-benzonitrile | 540 | 541 [M + H]+ | +++ |
| 63 | 4-{4-[4-(3-Trifluoromethyl-phenyl)-piperazine-1-carbonyl]-thiazol-2-yl}-piperazine-1-carboxylic acid tert-butyl ester | 525 | 526 [M + H]+ | ++ |

-continued

| Cp. | Name | Mass | LC/(+)-ESI-MS: | Biological activity[1] |
|---|---|---|---|---|
| 64 | (2-Piperazin-1-yl-thiazol-4-yl)-[4-(3-trifluoromethyl-phenyl)-piperazin-1-yl]-methanone | 425 | 426 [M + H]+ | + |
| 65 | {2-[4-(2-Methoxy-phenyl)-piperazin-1-yl]-thiazol-4-yl}-[4-(3-trifluoromethyl-phenyl)-piperazin-1-yl]-methanone | 531 | 532 [M + H]+ | ++ |
| 66 | 1-[4-(4-{4-[4-(3-Trifluoromethyl-phenyl)-piperazine-1-carbonyl]-thiazol-2-yl}-piperazin-1-yl)-phenyl]-ethanone | 543 | 544 [M + H]+ | ++ |
| 67 | [4-(3-Trifluoromethyl-phenyl)-piperazin-1-yl]-{2-[4-(3-trifluoromethyl-phenyl)-piperazin-1-yl]-thiazol-4-yl}-methanone | 569 | 570 [M + H]+ | + |
| 68 | [2-(4-Phenyl-piperazin-1-yl)-thiazol-4-yl]-[4-(3-trifluoromethyl-phenyl)-piperazin-1-yl]-methanone | 501 | 502 [M + H]+ | + |
| 69 | {2-[4-(4-Fluoro-phenyl)-piperazin-1-yl]-thiazol-4-yl}-[4-(3-trifluoromethyl-phenyl)-piperazin-1-yl]-methanone | 519 | 520 [M + H]+ | ++ |
| 70 | 4-(4-{4-[4-(3-Trifluoromethyl-phenyl)-piperazine-1-carbonyl]-thiazol-2-yl}-piperidine-1-carbonyl)-benzonitrile | 553 | 554 [M + H]+ | ++ |
| 71 | (4-Benzhydryl-piperazin-1-yl)-[2-(4-benzyl-piperazin-1-yl)-thiazol-4-yl]-methanone | 537 | 538 [M + H]+ | +++ |
| 72 | [2-(4-Benzyl-piperazin-1-yl)-thiazol-4-yl]-[4-(3-trifluoromethyl-phenyl)-piperazin-1-yl]-methanone | 515 | 516 [M + H]+ | +++ |
| 73 | 4-{4-[4-(3-Trifluoromethyl-phenyl)-piperazine-1-carbonyl]-thiazol-2-yl}-piperidine-1-carboxylic acid phenyl amide | 543 | 544 [M + H]+ | ++ |
| 74 | 4-{4-[4-(3-Trifluoromethyl-phenyl)-piperazine-1-carbonyl]-thiazol-2-yl}-piperidine-1-carboxylic acid (7-fluoro-2,3-dihydro-benzo[1,4]dioxin-5-yl)-amide | 619 | 620 [M + H]+ | ++ |
| 75 | 4-{4-[4-(3-Trifluoromethyl-phenyl)-piperazine-1-carbonyl]-thiazol-2-yl}-piperidine-1-carboxylic acid (2,3-dihydro-benzo[1,4]dioxin-6-yl)-amide | 601 | 602 [M + H]+ | ++ |
| 76 | 4-{4-[4-(3-Trifluoromethyl-phenyl)-piperazine-1-carbonyl]-thiazol-2-yl}-piperidine-1-carboxylic acid (5-methyl-2-trifluoromethyl-furan-3-yl)-amide | 615 | 616 [M + H]+ | ++ |
| 77 | 4-{4-[4-(3-Trifluoromethyl-phenyl)-piperazine-1-carbonyl]-thiazol-2-yl}-piperidine-1-carboxylic acid (2-thiophen-2-yl-ethyl)-amide | 577 | 578 [M + H]+ | +++ |
| 78 | 4-{4-[4-(3-Trifluoromethyl-phenyl)-piperazine-1-carbonyl]-thiazol-2-yl}-piperidine-1-carboxylic acid isopropylamide | 509 | 510 [M + H]+ | + |
| 79 | 4-{4-[4-(3-Trifluoromethyl-phenyl)-piperazine-1-carbonyl]-thiazol-2-yl}-piperidine-1-carboxylic acid (2-trifluoromethoxy-phenyl)-amide | 627 | 628 [M + H]+ | +++ |
| 80 | 4-{4-[4-(3-Trifluoromethyl-phenyl)-piperazine-1-carbonyl]-thiazol-2-yl}-piperidine-1-carboxylic acid (3-methoxy-phenyl)-amide | 573 | 574 [M + H]+ | + |
| 81 | 4-{4-[4-(3-Trifluoromethyl-phenyl)-piperazine-1-carbonyl]-thiazol-2-yl}-piperidine-1-carboxylic acid (3,4,5-trimethoxy-phenyl)-amide | 633 | 634 [M + H]+ | ++ |
| 82 | N-{4-[N'-(1H-Benzoimidazol-2-yl)-guanidinocarbonyl]-thiazol-2-yl}-2-trifluoromethoxy-benzamide | 489 | 490 [M + H]+ | +++ |
| 83 | 2-[1-(2-Trifluoromethoxy-benzoyl)-piperidin-4-yl]-thiazole-4-carboxylic acid (4-amino-6-oxo-1,6-dihydro-pyrimidin-2-yl)-amide | 508 | 509 [M + H]+ | + |
| 84 | 2-[1-(2-Trifluoromethoxy-benzoyl)-piperidin-4-yl]-thiazole-4-carboxylic acid (5-benzyl-4H-[1,2,4]triazol-3-yl)-amide | 556 | 557 [M + H]+ | + |
| 85 | 2-[1-(2-Trifluoromethoxy-benzoyl)-piperidin-4-yl]-thiazole-4-carboxylic acid (2-dimethylamino-6-oxo-1,6-dihydro-pyrimidin-4-yl)-amide | 536 | 537 [M + H]+ | + |

-continued

| Cp. | Name | Mass | LC/(+)-ESI-MS: | Biological activity[1] |
|---|---|---|---|---|
| 86 | 2-[1-(2-Trifluoromethoxy-benzoyl)-piperidin-4-yl]-thiazole-4-carboxylic acid (4-methyl-6-oxo-1,6-dihydro-pyrimidin-2-yl)-amide | 507 | 508 [M + H]+ | + |
| 87 | 2-[1-(2-Trifluoromethoxy-benzoyl)-piperidin-4-yl]-thiazole-4-carboxylic acid [5-(propane-1-sulfonyl)-1H-benzoimidazol-2-yl]-amide | 621 | 622 [M + H]+ | +++ |
| 88 | 2-[1-(2-Trifluoromethoxy-benzoyl)-piperidin-4-yl]-thiazole-4-carboxylic acid (4-dimethylamino-[1,3,5]triazin-2-yl)-amide | 521 | 522 [M + H]+ | + |
| 89 | 2-[1-(2-Trifluoromethoxy-benzoyl)-piperidin-4-yl]-thiazole-4-carboxylic acid (5-amino-1H-[1,2,4]triazol-3-yl)-amide | 481 | 482 [M + H]+ | + |
| 90 | N-Cyano-N'-{2-[1-(2-trifluoromethoxy-benzoyl)-piperidin-4-yl]-thiazole-4-carbonyl}-guanidine | 466 | 467 [M + H]+ | + |
| 91 | N-(1H-Benzoimidazol-2-yl)-N'-(2-morpholin-4-yl-thiazole-4-carbonyl)-guanidine | 371 | 372 [M + H]+ | + |
| 92 | 4-{4-[N'-Acetyl-N''-(1-acetyl-1H-benzoimidazol-2-yl)-guanidinocarbonyl]-thiazol-2-yl}-piperidine-1-carboxylic acid tert-butyl ester | 553 | 554 [M + H]+ | +++ |
| 93 | N-(1H-Benzoimidazol-2-yl)-N'-[2-(1-diphenylacetyl-piperidin-4-yl)-thiazole-4-carbonyl]-guanidine | 563 | 564 [M + H]+ | + |
| 94 | N-(1H-Benzoimidazol-2-yl)-N'-(2-piperidin-4-yl-thiazole-4-carbonyl)-guanidine | 369 | 370 [M + H]+ | + |
| 95 | 4-{4-[N'-(1H-Benzoimidazol-2-yl)-guanidinocarbonyl]-thiazol-2-yl}-piperidine-1-carboxylic acid tert-butyl ester | 469 | 470 [M + H]+ | +++ |
| 96 | [4-(1H-Benzoimidazol-2-yl)-piperazin-1-yl]-{2-[1-(2-trifluoromethoxy-benzoyl)-piperidin-4-yl]-thiazol-4-yl}-methanone | 618 | 619 [M + H]+ | +++ |
| 97 | [4-(5-Methoxy-1H-benzoimidazol-2-yl)-piperazin-1-yl]-{2-[1-(2-trifluoromethoxy-benzoyl)-piperidin-4-yl]-thiazol-4-yl}-methanone | 583 | 584 [M + H]+ | + |
| 98 | {4-[1-(4-Fluoro-benzyl)-1H-benzoimidazol-2-yl]-piperazin-1-yl}-{2-[1-(2-trifluoromethoxy-benzoyl)-piperidin-4-yl]-thiazol-4-yl}-methanone | 692 | 693 [M + H]+ | +++ |
| 99 | 3-Fluoro-4-trifluoromethyl-N-(1-{4-[4-(3-trifluoromethyl-phenyl)-piperazine-1-carbonyl]-thiazol-2-yl}-piperidin-4-ylmethyl)-benzamide | 642 | 643 [M + H]+ | + |
| 100 | 3-Cyclopentyl-N-(1-{4-[4-(3-trifluoromethyl-phenyl)-piperazine-1-carbonyl]-thiazol-2-yl}-piperidin-4-ylmethyl)-propionamide | 576 | 577 [M + H]+ | + |
| 101 | 2-Trifluoromethoxy-N-(1-{4-[4-(3-trifluoromethyl-phenyl)-piperazine-1-carbonyl]-thiazol-2-yl}-piperidin-4-ylmethyl)-benzamide | 640 | 641 [M + H]+ | + |
| 102 | 4-Cyano-N-(1-{4-[4-(3-trifluoromethyl-phenyl)-piperazine-1-carbonyl]-thiazol-2-yl}-piperidin-4-ylmethyl)-benzamide | 581 | 582 [M + H]+ | + |
| 103 | 2-{5-Methyl-2-[1-(2-trifluoromethoxy-benzoyl)-piperidin-4-yl]-thiazol-4-yl}-1-[4-(3-trifluoromethyl-phenyl)-piperazin-1-yl]-ethanone | 640 | 641 [M + H]+ | ++ |
| 104 | N-(1H-Benzoimidazol-2-yl)-N'-{2-[1-(2-trifluoromethoxy-benzoyl)-piperidin-4-yl]-thiazole-4-carbonyl}-guanidine | 557 | 558 [M + H]+ | +++ |
| 105 | 2-[1-(2-Trifluoromethoxy-benzoyl)-piperidin-4-yl]-thiazole-4-carboxylic acid (1H-benzoimidazol-2-yl)-amide | 515 | 516 [M + H]+ | + |
| 106 | N-(5,6-Dimethyl-1H-benzoimidazol-2-yl)-2-{5-methyl-2-[1-(2-trifluoromethoxy-benzoyl)-piperidin-4-yl]-thiazol-4-yl}-acetamide | 571 | 572 [M + H]+ | + |
| 107 | [2-(1-Pyridin-4-ylmethyl-piperidin-4-yl)-thiazol-4-yl]-[4-(3-trifluoromethyl-phenyl)-piperazin-1-yl]-methanone | 515 | 516 [M + H]+ | + |

-continued

| Cp. | Name | Mass | LC/(+)-ESI-MS: | Biological activity[1] |
|---|---|---|---|---|
| 108 | [2-(1-Pyridin-3-ylmethyl-piperidin-4-yl)-thiazol-4-yl]-[4-(3-trifluoromethyl-phenyl)-piperazin-1-yl]-methanone | 446 | 447 [M + H]+ | + |
| 109 | {2-[1-(2-Trifluoromethoxy-benzyl)-piperidin-4-yl]-thiazol-4-yl}-[4-(3-trifluoromethyl-phenyl)-piperazin-1-yl]-methanone | 598 | 599 [M + H]+ | + |
| 110 | 2-[1-(2-Trifluoromethoxy-benzoyl)-piperidin-4-yl]-thiazole-4-carboxylic acid bis-(4-chloro-benzyl)-amide | 647 | 648 [M + H]+ | + |
| 111 | (4-Benzotriazol-1-yl-piperidin-1-yl)-{2-[1-(2-trifluoromethoxy-benzoyl)-piperidin-4-yl]-thiazol-4-yl}-methanone | 584 | 585 [M + H]+ | + |
| 112 | 4-(4-{4-[4-(3-Trifluoromethyl-phenyl)-piperazine-1-carbonyl]-thiazol-2-yl}-piperidin-1-yl)-benzonitrile | 525 | 526 [M + H]+ | + |
| 113 | 4-{4-[4-(3-Trifluoromethyl-phenyl)-piperazine-1-carbonyl]-thiazol-2-yl}-piperidine-1-carboxylic acid | 468 | 469 [M + H]+ | + |
| 114 | 4-(4-{4-[4-(3-Trifluoromethyl-phenyl)-piperazine-1-carbonyl]-thiazol-2-yl}-piperidine-1-carbonyl)-benzonitrile | 568 | 569 [M + H]+ | + |
| 115 | {2-[1-(3-Trifluoromethoxy-benzyl)-piperidin-4-yl]-thiazol-4-yl}-[4-(3-trifluoromethyl-phenyl)-piperazin-1-yl]-methanone | 598 | 599 [M + H]+ | ++ |
| 116 | {2-[1-(2,5-Dimethoxy-phenyl)-piperidin-4-yl]-thiazol-4-yl}-[4-(3-trifluoromethyl-phenyl)-piperazin-1-yl]-methanone | 560 | 560 [M + H]+ | + |
| 117 | {2-[1-(4-Methanesulfonyl-phenyl)-piperidin-4-yl]-thiazol-4-yl}-[4-(3-trifluoromethyl-phenyl)-piperazin-1-yl]-methanone | 578 | 579 [M + H]+ | + |
| 118 | [4-(3-Trifluoromethyl-phenyl)-piperazin-1-yl]-[2-(4'-trifluoromethyl-3,4,5,6-tetrahydro-2H-[1,2']bipyridinyl-4-yl)-thiazol-4-yl]-methanone | 569 | 570 [M + H]+ | + |
| 119 | [2-(1-Phenyl-piperidin-4-yl)-thiazol-4-yl]-[4-(3-trifluoromethyl-phenyl)-piperazin-1-yl]-methanone | 500 | 501 [M + H]+ | + |
| 120 | [2-(1-Benzyl-piperidin-4-yl)-thiazol-4-yl]-[4-(4,6-dimethoxy-[1,3,5]triazin-2-yl)-piperazin-1-yl]-methanone | 509 | 510 [M + H]+ | + |
| 121 | {2-[1-(4-Bromo-benzyl)-piperidin-4-yl]-thiazol-4-yl}-[4-(4,6-dimethoxy-[1,3,5]triazin-2-yl)-piperazin-1-yl]-methanone | 587 | 588 [M + H]+ | + |
| 122 | [2-(1-Pyrazin-2-yl-piperidin-4-yl)-thiazol-4-yl]-[4-(3-trifluoromethyl-phenyl)-piperazin-1-yl]-methanone | 502 | 503 [M + H]+ | + |
| 123 | [2-(3,4,5,6-Tetrahydro-2H-[1,2']bipyridinyl-4-yl)-thiazol-4-yl]-[4-(3-trifluoromethyl-phenyl)-piperazin-1-yl]-methanone | 501 | 502 [M + H]+ | ++ |
| 124 | (4-{4-[4-(2-Methylsulfanyl-pyrimidin-4-yl)-piperazine-1-carbonyl]-thiazol-2-yl}-piperidin-1-yl)-(2-trifluoromethoxy-phenyl)-methanone | 592 | 593 [M + H]+ | + |
| 125 | 4-[4-(3-Trifluoromethyl-phenyl)-piperazine-1-carbonyl]-piperidine-1-carboxylic acid tert-butyl ester | 441 | 442 [M + H]+ | + |
| 126 | 1-(4-{4-[4-(4,6-Dimethoxy-[1,3,5]triazin-2-yl)-piperazine-1-carbonyl]-thiazol-2-yl}-piperidin-1-yl)-2-(4-fluoro-phenyl)-ethanone | 555 | 556 [M + H]+ | + |
| 127 | [4-(4,6-Dimethoxy-[1,3,5]triazin-2-yl)-piperazin-1-yl]-{2-[1-(2-trifluoromethoxy-benzoyl)-piperidin-4-yl]-thiazol-4-yl}-methanone | 607 | 608 [M + H]+ | + |
| 128 | 1-[4-(3-Chloro-phenyl)-piperazin-1-yl]-2-{5-methyl-2-[1-(2-trifluoromethoxy-benzoyl)-piperidin-4-yl]-thiazol-4-yl}-ethanone | 606 | 607 [M + H]+ | +++ |
| 129 | (4-{4-[4-(7H-Purin-6-yl)-piperazine-1-carbonyl]-thiazol-2-yl}-piperidin-1-yl)-(2-trifluoromethoxy-phenyl)-methanone | 586 | 587 [M + H]+ | + |

-continued

| Cp. | Name | Mass | LC/(+)-ESI-MS: | Biological activity[1] |
|---|---|---|---|---|
| 130 | (4-{4-[4-(2,6-Dimethoxy-pyrimidin-4-yl)-piperazine-1-carbonyl]-thiazol-2-yl}-piperidin-1-yl)-(2-trifluoromethoxy-phenyl)-methanone | 606 | 607 [M + H]+ | + |
| 131 | 2-{1-[2-(4-Fluoro-phenyl)-acetyl]-piperidin-4-yl}-thiazole-4-carboxylic acid (5,6-dimethyl-1H-benzoimidazol-2-yl)-amide | 491 | 492 [M + H]+ | + |
| 132 | 2-{1-[5-(4-Chloro-phenyl)-2-trifluoromethyl-furan-3-carbonyl]-piperidin-4-yl}-thiazole-4-carboxylic acid (5,6-dimethyl-1H-benzoimidazol-2-yl)-amide | 627 | 628 [M + H]+ | + |
| 133 | 2-[1-(2-Trifluoromethoxy-benzoyl)-piperidin-4-yl]-thiazole-4-carboxylic acid (5,6-dimethyl-1H-benzoimidazol-2-yl)-amide | 543 | 544 [M + H]+ | +++ |
| 134 | 4-{4-[4-(3-Trifluoromethyl-phenyl)-piperazine-1-carbonyl]-thiazol-2-yl}-piperidine-1-carboxylic acid phenylamide | 543 | 544 [M + H]+ | + |
| 135 | 4-{4-[4-(3-Trifluoromethyl-phenyl)-piperazine-1-carbonyl]-thiazol-2-yl}-piperidine-1-carboxylic acid (7-fluoro-2,3-dihydro-benzo[1,4]dioxin-5-yl)-amide | 619 | 620 [M + H]+ | + |
| 136 | 4-{4-[4-(3-Trifluoromethyl-phenyl)-piperazine-1-carbonyl]-thiazol-2-yl}-piperidine-1-carboxylic acid (2,3-dihydro-benzo[1,4]dioxin-6-yl)-amide | 601 | 602 [M + H]+ | + |
| 137 | 4-{4-[4-(3-Trifluoromethyl-phenyl)-piperazine-1-carbonyl]-thiazol-2-yl}-piperidine-1-carboxylic acid (5-methyl-2-trifluoromethyl-furan-3-yl)-amide | 615 | 616 [M + H]+ | + |
| 138 | 4-{4-[4-(3-Trifluoromethyl-phenyl)-piperazine-1-carbonyl]-thiazol-2-yl}-piperidine-1-carboxylic acid (2-thiophen-2-yl-ethyl)-amide | 577 | 578 [M + H]+ | +++ |
| 139 | 4-{4-[4-(3-Trifluoromethyl-phenyl)-piperazine-1-carbonyl]-thiazol-2-yl}-piperidine-1-carboxylic acid isopropylamide | 509 | 510 [M + H]+ | + |
| 140 | 4-{4-[4-(3-Trifluoromethyl-phenyl)-piperazine-1-carbonyl]-thiazol-2-yl}-piperidine-1-carboxylic acid (2-trifluoromethoxy-phenyl)-amide | 627 | 628 [M + H]+ | + |
| 141 | 4-{4-[4-(3-Trifluoromethyl-phenyl)-piperazine-1-carbonyl]-thiazol-2-yl}-piperidine-1-carboxylic acid (3-methoxy-phenyl)-amide | 573 | 574 [M + H]+ | + |
| 142 | 4-{4-[4-(3-Trifluoromethyl-phenyl)-piperazine-1-carbonyl]-thiazol-2-yl}-piperidine-1-carboxylic acid (3-fluoro-phenyl)-amide | 561 | 562 [M + H]+ | ++ |
| 143 | 4-{4-[4-(3-Trifluoromethyl-phenyl)-piperazine-1-carbonyl]-thiazol-2-yl}-piperidine-1-carboxylic acid (4-fluoro-phenyl)-amide | 561 | 562 [M + H]+ | + |
| 144 | 2-Piperidin-4-yl-thiazole-4-carboxylic acid (5,6-dimethyl-1H-benzoimidazol-2-yl)-amide | 355 | 356 [M + H]+ | + |
| 145 | 2-[1-(2-Trifluoromethoxy-benzoyl)-piperidin-4-yl]-thiazole-4-carboxylic acid [1-(1H-indol-2-yl)-ethyl]-methyl-amide | 556 | 557 [M + H]+ | + |
| 146 | (2-Phenyl-morpholin-4-yl)-{2-[1-(2-trifluoromethoxy-benzoyl)-piperidin-4-yl]-thiazol-4-yl}-methanone | 545 | 546 [M + H]+ | + |
| 147 | 2-[1-(2-Trifluoromethoxy-benzoyl)-piperidin-4-yl]-thiazole-4-carboxylic acid methyl-(morpholin-4-yl-1-phenyl-ethyl)-amide | 602 | 603 [M + H]+ | + |
| 148 | 2-[1-(2-Trifluoromethoxy-benzoyl)-piperidin-4-yl]-thiazole-4-carboxylic acid benzyl-(2-hydroxy-ethyl)-amide | 533 | 534 [M + H]+ | ++ |
| 149 | 2-[1-(2-Trifluoromethoxy-benzoyl)-piperidin-4-yl]-thiazole-4-carboxylic acid benzyl-phenethyl-amide | 593 | 594 [M + H]+ | + |

-continued

| Cp. | Name | Mass | LC/(+)-ESI-MS: | Biological activity[1] |
|---|---|---|---|---|
| 150 | [1-(5-Chloro-2-methylamino-phenyl)-3,4-dihydro-1H-isoquinolin-2-yl]-{2-[1-(2-trifluoromethoxy-benzoyl)-piperidin-4-yl]-thiazol-4-yl}-methanone | 654 | 655 [M + H]+ | ++ |
| 151 | (4-{4-[4-(3-Chloro-phenyl)-piperazine-1-carbonyl]-thiazol-2-yl}-piperidin-1-yl)-(2-trifluoromethyl-phenyl)-methanone | 578 | 579 [M + H]+ | + |
| 152 | [4-(4,6-Dimethoxy-[1,3,5]triazin-2-yl)-piperazin-1-yl]-(2-piperidin-4-yl-thiazol-4-yl)-methanone | 419 | 420 [M + H]+ | ++ |
| 153 | {2-[1-(2,4-Dimethoxy-phenyl)-piperidin-4-yl]-thiazol-4-yl}-[4-(3-trifluoromethyl-phenyl)-piperazin-1-yl]-methanone | 560 | 561 [M + H]+ | + |
| 154 | {2-[1-(4-Trifluoromethoxy-phenyl)-piperidin-4-yl]-thiazol-4-yl}-[4-(3-trifluoromethyl-phenyl)-piperazin-1-yl]-methanone | 584 | 585 [M + H]+ | + |
| 155 | [4-(3-Trifluoromethyl-phenyl)-piperazin-1-yl]-{2-[1-(4-trifluoromethyl-phenyl)-piperidin-4-yl]-thiazol-4-yl}-methanone | 568 | 569 [M + H]+ | + |
| 156 | [2-(1-Benzo[1,3]dioxol-5-yl-piperidin-4-yl)-thiazol-4-yl]-[4-(3-trifluoromethyl-phenyl)-piperazin-1-yl]-methanone | 544 | 545 [M + H]+ | + |
| 157 | {2-[1-(2,3-Dihydro-benzo[1,4]dioxin-6-yl)-piperidin-4-yl]-thiazol-4-yl}-[4-(3-trifluoromethyl-phenyl)-piperazin-1-yl]-methanone | 558 | 559 [M + H]+ | + |
| 158 | {2-[1-(2-Methoxy-phenyl)-piperidin-4-yl]-thiazol-4-yl}-[4-(3-trifluoromethyl-phenyl)-piperazin-1-yl]-methanone | 530 | 531 [M + H]+ | + |
| 159 | {2-[1-(3,4-Dimethoxy-phenyl)-piperidin-4-yl]-thiazol-4-yl}-[4-(3-trifluoromethyl-phenyl)-piperazin-1-yl]-methanone | 560 | 561 [M + H]+ | + |
| 160 | 1-{4-[4-(6,7-Dihydroxy-3,4-dihydro-1H-isoquinoline-2-carbonyl)-thiazol-2-yl]-piperidin-1-yl}-2-(4-fluoro-phenyl)-ethanone | 495 | 496 [M + H]+ | + |
| 161 | 1-{4-[4-(6,7-Dimethoxy-3,4-dihydro-1H-isoquinoline-2-carbonyl)-thiazol-2-yl]-piperidin-1-yl}-2-(4-fluoro-phenyl)-ethanone | 523 | 524 [M + H]+ | + |
| 162 | 1-{4-[4-(2,3-Dihydro-indole-1-carbonyl)-thiazol-2-yl]-piperidin-1-yl}-2-(4-fluoro-phenyl)-ethanone | 449 | 450 [M + H]+ | + |
| 163 | 1-{4-[4-(3,4-Dihydro-1H-isoquinoline-2-carbonyl)-thiazol-2-yl]-piperidin-1-yl}-2-(4-fluoro-phenyl)-ethanone | 463 | 464 [M + H]+ | + |
| 164 | {2-[1-(2,6-Dimethoxy-pyrimidin-4-yl)-piperidin-4-yl]-thiazol-4-yl}-[4-(3-trifluoromethyl-phenyl)-piperazin-1-yl]-methanone | 562 | 563 [M + H]+ | ++ |
| 165 | {2-[1-(2-Bromo-benzyl)-piperidin-4-yl]-thiazol-4-yl}-[4-(3-trifluoromethyl-phenyl)-piperazin-1-yl]-methanone | 592 | 593 [M + H]+ | + |
| 166 | 4-(4-{4-[4-(3-Trifluoromethyl-phenyl)-piperazine-1-carbonyl]-thiazol-2-yl}-piperidin-1-ylmethyl)-benzonitrile | 539 | 540 [M + H]+ | + |
| 167 | [2-(1-Biphenyl-4-ylmethyl-piperidin-4-yl)-thiazol-4-yl]-[4-(3-trifluoromethyl-phenyl)-piperazin-1-yl]-methanone | 590 | 591 [M + H]+ | + |
| 168 | {2-[1-(2,6-Difluoro-benzyl)-piperidin-4-yl]-thiazol-4-yl}-[4-(3-trifluoromethyl-phenyl)-piperazin-1-yl]-methanone | 550 | 551 [M + H]+ | + |
| 169 | {2-[1-(4-Trifluoromethyl-benzyl)-piperidin-4-yl]-thiazol-4-yl}-[4-(3-trifluoromethyl-phenyl)-piperazin-1-yl]-methanone | 582 | 583 [M + H]+ | + |
| 170 | {2-[1-(4-Fluoro-benzyl)-piperidin-4-yl]-thiazol-4-yl}-[4-(3-trifluoromethyl-phenyl)-piperazin-1-yl]-methanone | 532 | 533 [M + H]+ | + |
| 171 | {2-[1-(2-Chloro-4-fluoro-benzyl)-piperidin-4-yl]-thiazol-4-yl}-[4-(3-trifluoromethyl-phenyl)-piperazin-1-yl]-methanone | 566 | 567 [M + H]+ | + |
| 172 | {2-[1-(4-Trifluoromethoxy-benzyl)-piperidin-4-yl]-thiazol-4-yl}-[4-(3-trifluoromethyl-phenyl)-piperazin-1-yl]-methanone | 598 | 599 [M + H]+ | + |

-continued

| Cp. | Name | Mass | LC/(+)-ESI-MS: | Biological activity[1] |
|---|---|---|---|---|
| 173 | {2-[1-(3-Methoxy-benzyl)-piperidin-4-yl]-thiazol-4-yl}-[4-(3-trifluoromethyl-phenyl)-piperazin-1-yl]-methanone | 544 | 545 [M + H]+ | + |
| 174 | {2-[1-(4-Bromo-benzyl)-piperidin-4-yl]-thiazol-4-yl}-[4-(3-trifluoromethyl-phenyl)-piperazin-1-yl]-methanone | 592 | 593 [M + H]+ | + |
| 175 | {2-[1-(3,5-Bis-trifluoromethyl-benzyl)-piperidin-4-yl-thiazol-4-yl]-[4-(3-trifluoromethyl-phenyl)-piperazin-1-yl]-methanone | 650 | 651 [M + H]+ | + |
| 176 | {2-[1-(4,6-Dimethoxy-[1,3,5]triazin-2-yl)-piperidin-4-yl]-thiazol-4-yl}-[4-(3-trifluoromethyl-phenyl)-piperazin-1-yl]-methanone | 563 | 564 [M + H]+ | + |
| 177 | [2-(1-Benzyl-piperidin-4-yl)-thiazol-4-yl]-[4-(3-trifluoromethyl-phenyl)-piperazin-1-yl]-methanone | 514 | 515 [M + H]+ | + |
| 178 | {2-[1-(3-Methoxy-phenyl)-piperidin-4-yl]-thiazol-4-yl}-[4-(3-trifluoromethyl-phenyl)-piperazin-1-yl]-methanone | 530 | 531 [M + H]+ | + |
| 179 | 2-(2-{1-[2-(4-Fluoro-phenyl)-acetyl]-piperidin-4-yl}-thiazole-4-carbonyl)-7-hydroxy-1,2,3,4-tetrahydro-isoquinoline-3-carboxylic acid methyl ester | 537 | 538 [M + H]+ | + |
| 180 | 2-(4-Fluoro-phenyl)-1-{4-[4-(4-phenyl-piperazine-1-carbonyl)-thiazol-2-yl]-piperidin-1-yl}-ethanone | 492 | 493 [M + H]+ | + |
| 181 | 2-(4-Fluoro-phenyl)-1-(4-{4-[5-trifluoromethyl-benzotriazol-1-yl)-piperidine-1-carbonyl]-thiazol-2-yl}-piperidin-1-yl)-ethanone | 600 | 601 [M + H]+ | + |
| 182 | 1-{4-[4-(4-Benzotriazol-1-yl-piperidine-1-carbonyl)-thiazol-2-yl]-piperidin-1-yl}-2-(4-fluoro-phenyl)-ethanone | 532 | 533 [M + H]+ | + |
| 183 | 2-(4-{4-[4-(3-Trifluoromethyl-phenyl)-piperazine-1-carbonyl]-thiazol-2-yl}-piperidine-1-carbonyl)-nicotinic acid | 573 | 574 [M + H]+ | + |
| 184 | 2-(4-{4-[4-(3-Trifluoromethyl-phenyl)-piperazine-1-carbonyl]-thiazol-2-yl}-piperidine-1-carbonyl)-terephthalic acid | 616 | 617 [M + H]+ | + |
| 185 | 2-(4-{4-[4-(3-Trifluoromethyl-phenyl)-piperazine-1-carbonyl]-thiazol-2-yl}-piperidine-1-carbonyl)-benzoic acid | 572 | 573 [M + H]+ | + |
| 186 | 3-Hydroxy-2-(4-{4-[4-(3-trifluoromethyl-phenyl)-piperazine-1-carbonyl]-thiazol-2-yl}-piperidine-1-carbonyl)-benzoic acid | 588 | 589 [M + H]+ | + |
| 187 | 4,5-Dichloro-2-(4-{4-[4-(3-trifluoromethyl-phenyl)-piperazine-1-carbonyl]-thiazol-2-yl}-piperidine-1-carbonyl)-benzoic acid | 640 | 641 [M + H]+ | + |
| 188 | 2-(4-{4-[4-(3-Trifluoromethyl-phenyl)-piperazine-1-carbonyl]-thiazol-2-yl}-piperidine-1-carbonyl)-cyclopent-1-enecarboxylic acid | 562 | 563 [M + H]+ | + |
| 189 | 2-(4-{4-[4-(3-Trifluoromethyl-phenyl)-piperazine-1-carbonyl]-thiazol-2-yl}-piperidine-1-carbonyl)-cyclohexanecarboxylic acid | 578 | 579 [M + H]+ | + |
| 190 | 2-(4-{4-[4-(3-Trifluoromethyl-phenyl)-piperazine-1-carbonyl]-thiazol-2-yl}-piperidine-1-carbonyl)-cyclohex-1-enecarboxylic acid | 576 | 577 [M + H]+ | + |
| 191 | 4-Oxo-4-(4-{4-[4-(3-trifluoromethyl-phenyl)-piperazine-1-carbonyl]-thiazol-2-yl}-piperidin-1-yl)-but-2-enoic acid | 522 | 523 [M + H]+ | + |
| 192 | {2-[1-(3,5-Dimethyl-isoxazole-4-sulfonyl)-piperidin-4-yl]-thiazol-4-yl}-[4-(3-trifluoromethyl-phenyl)-piperazin-1-yl]-methanone | 583 | 584 [M + H]+ | + |
| 193 | [2-(1-Pentafluorobenzenesulfonyl-piperidin-4-yl)-thiazol-4-yl]-[4-(3-trifluoromethyl-phenyl)-piperazin-1-yl]-methanone | 654 | 655 [M + H]+ | + |
| 194 | {2-[1-(Thiophene-2-sulfonyl)-piperidin-4-yl]-thiazol-4-yl}-[4-(3-trifluoromethyl-phenyl)-piperazin-1-yl]-methanone | 570 | 571 [M + H]+ | + |

-continued

| Cp. | Name | Mass | LC/(+)-ESI-MS: | Biological activity[1] |
|---|---|---|---|---|
| 195 | {2-[1-(2-Chloro-4-fluoro-benzenesulfonyl)-piperidin-4-yl]-thiazol-4-yl}-[4-(3-trifluoromethyl-phenyl)-piperazin-1-yl]-methanone | 616 | 617 [M + H]+ | + |
| 196 | {2-[1-(2-Bromo-benzenesulfonyl)-piperidin-4-yl]-thiazol-4-yl}-[4-(3-trifluoromethyl-phenyl)-piperazin-1-yl]-methanone | 642 | 643 [M + H]+ | + |
| 197 | {2-[1-(6-Chloro-imidazo[2,1-b]thiazole-5-sulfonyl)-piperidin-4-yl]-thiazol-4-yl}-[4-(3-trifluoromethyl-phenyl)-piperazin-1-yl]-methanone | 644 | 645 [M + H]+ | + |
| 198 | [2-(1-Phenylmethanesulfonyl-piperidin-4-yl)-thiazol-4-yl]-[4-(3-trifluoromethyl-phenyl)-piperazin-1-yl]-methanone | 578 | 579 [M + H]+ | + |
| 199 | {2-[1-(4-Bromo-benzenesulfonyl)-piperidin-4-yl]-thiazol-4-yl}-[4-(3-trifluoromethyl-phenyl)-piperazin-1-yl]-methanone | 642 | 643 [M + H]+ | + |
| 200 | {2-[1-(2,4-Dichloro-benzenesulfonyl)-piperidin-4-yl]-thiazol-4-yl}-[4-(3-trifluoromethyl-phenyl)-piperazin-1-yl]-methanone | 632 | 633 [M + H]+ | × |
| 201 | {2-[1-(3,5-Bis-trifluoromethyl-benzenesulfonyl)-piperidin-4-yl]-thiazol-4-yl}-[4-(3-trifluoromethyl-phenyl)-piperazin-1-yl]-methanone | 700 | 701 [M + H]+ | ++ |
| 202 | {2-[1-(5-Chloro-2-methoxy-benzenesulfonyl)-piperidin-4-yl]-thiazol-4-yl}-[4-(3-trifluoromethyl-phenyl)-piperazin-1-yl]-methanone | 628 | 629 [M + H]+ | ++ |
| 203 | {2-[1-(5-Bromo-thiophene-2-sulfonyl)-piperidin-4-yl]-thiazol-4-yl}-[4-(3-trifluoromethyl-phenyl)-piperazin-1-yl]-methanone | 648 | 649 [M + H]+ | + |
| 204 | {2-[1-(Toluene-4-sulfonyl)-piperidin-4-yl]-thiazol-4-yl}-[4-(3-trifluoromethyl-phenyl)-piperazin-1-yl]-methanone | 578 | 579 [M + H]+ | + |
| 205 | {2-[1-(4-Trifluoromethoxy-benzenesulfonyl)-piperidin-4-yl]-thiazol-4-yl}-[4-(3-trifluoromethyl-phenyl)-piperazin-1-yl]-methanone | 648 | 649 [M + H]+ | + |
| 206 | {2-[1-(4-Chloro-benzenesulfonyl)-piperidin-4-yl]-thiazol-4-yl}-[4-(3-trifluoromethyl-phenyl)-piperazin-1-yl]-methanone | 598 | 599 [M + H]+ | + |
| 207 | N-[4-(4-{4-[4-(3-Trifluoromethyl-phenyl)-piperazine-1-carbonyl]-thiazol-2-yl}-piperidine-1-sulfonyl)-phenyl]-acetamide | 621 | 622 [M + H]+ | + |
| 208 | [2-(1-Benzenesulfonyl-piperidin-4-yl)-thiazol-4-yl]-[4-(3-trifluoromethyl-phenyl)-piperazin-1-yl]-methanone | 564 | 565 [M + H]+ | + |
| 209 | {2-[1-(3-Methoxy-benzoyl)-piperidin-4-yl]-thiazol-4-yl}-[4-(3-trifluoromethyl-phenyl)-piperazin-1-yl]-methanone | 558 | 559 [M + H]+ | + |
| 210 | {2-[1-(4-Methyl-3,4-dihydro-2H-benzo[1,4]oxazine-7-carbonyl)-piperidin-4-yl]-thiazol-4-yl}-[4-(3-trifluoromethyl-phenyl)-piperazin-1-yl]-methanone | 599 | 600 [M + H]+ | ++ |
| 211 | {2-[1-(Quinoxaline-6-carbonyl)-piperidin-4-yl]-thiazol-4-yl}-[4-(3-trifluoromethyl-phenyl)-piperazin-1-yl]-methanone | 580 | 581 [M + H]+ | + |
| 212 | {2-[1-(Thiophene-2-carbonyl)-piperidin-4-yl]-thiazol-4-yl}-[4-(3-trifluoromethyl-phenyl)-piperazin-1-yl]-methanone | 534 | 535 [M + H]+ | + |
| 213 | {2-[1-(Benzo[b]thiophene-2-carbonyl)-piperidin-4-yl]-thiazol-4-yl}-[4-(3-trifluoromethyl-phenyl)-piperazin-1-yl]-methanone | 584 | 585 [M + H]+ | ++ |
| 214 | 3-Phenyl-1-(4-{4-[4-(3-trifluoromethyl-phenyl)-piperazine-1-carbonyl]-thiazol-2-yl}-piperidin-1-yl)-propenone | 554 | 555 [M + H]+ | ++ |
| 215 | {2-[1-(3-Fluoro-4-trifluoromethyl-benzoyl)-piperidin-4-yl]-thiazol-4-yl}-[4-(3-trifluoromethyl-phenyl)-piperazin-1-yl]-methanone | 614 | 615 [M + H]+ | +++ |

-continued

| Cp. | Name | Mass | LC/(+)-ESI-MS: | Biological activity[1] |
|---|---|---|---|---|
| 216 | {2-[1-(5-tert-Butyl-2-methyl-2H-pyrazole-3-carbonyl)-piperidin-4-yl]-thiazol-4-yl}-[4-(3-trifluoromethyl-phenyl)-piperazin-1-yl]-methanone | 588 | 589 [M + H]+ | ++ |
| 217 | {2-[1-(2,3-Dihydro-benzo[1,4]dioxine-2-carbonyl)-piperidin-4-yl]-thiazol-4-yl}[4-(3-trifluoromethyl-phenyl)-piperazin-1-yl]-methanone | 586 | 587 [M + H]+ | +++ |
| 218 | (2-{1-[5-(4-Chloro-phenyl)-2-trifluoromethyl-furan-3-carbonyl]-piperidin-4-yl}-thiazol-4-yl)-[4-(3-trifluoromethyl-phenyl)-piperazin-1-yl]-methanone | 696 | 697 [M + H]+ | +++ |
| 219 | {2-[1-(3,5-Dimethyl-isoxazole-4-carbonyl)-piperidin-4-yl]-thiazol-4-yl}-[4-(3-trifluoromethyl-phenyl)-piperazin-1-yl]-methanone | 547 | 548 [M + H]+ | + |
| 220 | (2-{1-[4-(4-Chloro-benzenesulfonyl)-3-methyl-thiophene-2-carbonyl]-piperidin-4-yl}-thiazol-4-yl)-[4-(3-trifluoromethyl-phenyl)-piperazin-1-yl]-methanone | 722 | 723 [M + H]+ | + |
| 221 | {2-[1-(4-Methyl-[1,2,3]thiadiazole-5-carbonyl)-piperidin-4-yl]-thiazol-4-yl}-[4-(3-trifluoromethyl-phenyl)-piperazin-1-yl]-methanone | 550 | 551 [M + H]+ | + |
| 222 | {2-[1-(Pyridine-3-carbonyl)-piperidin-4-yl]-thiazol-4-yl}-[4-(3-trifluoromethyl-phenyl)-piperazin-1-yl]-methanone | 529 | 530 [M + H]+ | + |
| 223 | {2-[1-(2-Trifluoromethoxy-benzoyl)-piperidin-4-yl]-thiazol-4-yl}-[4-(3-trifluoromethyl-phenyl)-piperazin-1-yl]-methanone | 612 | 613 [M + H]+ | +++ |
| 224 | 3-Cyclopentyl-1-(4-{4-[4-(3-trifluoromethyl-phenyl)-piperazine-1-carbonyl]-thiazol-2-yl}-piperidin-1-yl)-propan-1-one | 548 | 549 [M + H]+ | + |
| 225 | [4-(3-Trifluoromethyl-phenyl)-piperazin-1-yl]-{2-[1-(3,4,5-trimethoxy-benzoyl)-piperidin-4-yl]-thiazol-4-yl}-methanone | 618 | 619 [M + H]+ | + |
| 226 | {2-[1-(3-Dimethylamino-benzoyl)-piperidin-4-yl]-thiazol-4-yl}-[4-(3-trifluoromethyl-phenyl)-piperazin-1-yl]-methanone | 571 | 572 [M + H]+ | ++ |
| 227 | [2-(2-{1-[2-(4-Fluoro-phenyl)-acetyl]-piperidin-4-yl}-thiazole-4-carbonyl)-1,2,3,4-tetrahydro-isoquinolin-1-yl]-acetic acid methyl ester | 535 | 536 [M + H]+ | + |
| 228 | 1-(2-{1-[2-(4-Fluoro-phenyl)-acetyl]-piperidin-4-yl}-thiazole-4-carbonyl)-4-phenyl-piperidine-4-carbonitrile | 516 | 517 [M + H]+ | + |
| 229 | 2-(4-Fluoro-phenyl)-1-(4-{4-[4-(2-methoxy-phenyl)-piperazine-1-carbonyl]-thiazol-2-yl}-piperidin-1-yl)-ethanone | 511 | 523 [M + H]+ | + |
| 230 | {2-[1-(Furan-2-carbonyl)-piperidin-4-yl]-thiazol-4-yl}-[4-(3-trifluoromethyl-phenyl)-piperazin-1-yl]-methanone | 518 | 519 [M + H]+ | + |
| 231 | 1-{4-[4-(4-Butyl-piperazine-1-carbonyl)-thiazol-2-yl]-piperidin-1-yl}-2-(4-fluoro-phenyl)-ethanone | 472 | 473 [M + H]+ | + |
| 232 | 1-{4-[4-(6,7-Dimethoxy-3-methyl-3,4-dihydro-1H-isoquinoline-2-carbonyl)-thiazol-2-yl]-piperidin-1-yl}-2-(4-fluoro-phenyl)-ethanone | 537 | 538 [M + H]+ | + |
| 233 | 1-{4-[4-(6,7-Dihydroxy-1-methyl-3,4-dihydro-1H-isoquinoline-2-carbonyl)-thiazol-2-yl]-piperidin-1-yl}-2-(4-fluoro-phenyl)-ethanone | 509 | 510 [M + H]+ | + |
| 234 | 1-{4-[4-(6,7-Dimethoxy-1-methyl-3,4-dihydro-1H-isoquinoline-2-carbonyl)-thiazol-2-yl]-piperidin-1-yl}-2-(4-fluoro-phenyl)-ethanone | 537 | 538 [M + H]+ | + |
| 235 | 1-(4-{4-[1-(5-Chloro-2-methylamino-phenyl)-3,4-dihydro-1H-isoquinoline-2-carbonyl]-thiazol-2-yl}-piperidin-1-yl)-2-(4-fluoro-phenyl)-ethanone | 602 | 603 [M + H]+ | + |

-continued

| Cp. | Name | Mass | LC/(+)-ESI-MS: | Biological activity[1] |
|---|---|---|---|---|
| 236 | 2-(4-Fluoro-phenyl)-1-(4-{4-[2-(4-fluoro-phenyl)-pyrrolidine-1-carbonyl]-thiazol-2-yl}-piperidin-1-yl)-ethanone | 495 | 496 [M + H]$^+$ | + |
| 237 | 2-(4-Fluoro-phenyl)-1-{4-[4-(4-pyridin-2-yl-piperazine-1-carbonyl)-thiazol-2-yl]-piperidin-1-yl}-ethanone | 493 | 494 [M + H]$^+$ | + |
| 238 | 1-(4-{4-[4-(3-Chloro-phenyl)-piperazine-1-carbonyl]-thiazol-2-yl}-piperidin-1-yl)-2-(4-fluoro-phenyl)-ethanone | 526 | 527 [M + H]$^+$ | + |
| 239 | {2-[1-(2,5-Dimethoxy-phenyl)-piperidin-4-yl]-thiazol-4-yl}-[4-(3-trifluoromethyl-phenyl)-piperazin-1-yl]-methanone | 560 | 561 [M + H]$^+$ | + |
| 240 | 4-{4-[4-(3-Trifluoromethyl-phenyl)-piperazine-1-carbonyl]-thiazol-2-yl}-piperidine-1-carboxylic acid (3,4,5-trimethoxy-phenyl)-amide | 633 | 634 [M + H]$^+$ | ++ |

[1] The biological data refer to results obtained from the NF-κB inflammation assay. ["+" stands for 50-80% inhibition, "++" means 80-90% and "+++" stands for 90-100% inhibition]

Proteasome Assay:

The chymotryptic activity of the 20S proteasome (Immatics, Tübingen) was determined using a Tecan Ultra plate reader and Suc-LLVT-AMC as substrate (Bachem). In the wells of a black 96 well polypropylene plate, 2 µl of the respective inhibitor dissolved in DMSO were mixed with 50 µl substrate solution (25 mM HEPES pH 7.5 at 20° C., 0.5 mM EDTA and Suc-LLVT-AMC (in the appropriate concentration) and the reaction was initiated by adding 150 µl proteasome solution (1.3 µg/ml 20S proteasome in 25 mM HEPES pH 7.5 at 20° C., 0.5 mM EDTA, 0.033% (w/v) SDS). Substrate hydrolysis was followed by fluorescence spectroscopy (excitation wavelength: 360 nm; emission wavelength: 465 nm) for 20 min at 30° C. and initial velocities were calculated and expressed as change in relative fluorescence units (RFU) per second.

For the determination of the $IC_{50}$ values (concentration of inhibitor required for 50% inhibition) at least four different inhibitor concentrations were applied. Each data point was recorded in triplicates. Curves were fitted with the a suitable program.

The Compounds have average activities between 1 and 30 µM

T-Lymphocyte Proliferation Assay:

Inhibition of Stimulated Peripheral Blood Monocytes (PBMC).

PBMCs were isolated from the blood of healthy volunteers with the help of ACCUSPIN™ System Histopaque®-1077 tubes, washed and resuspended with 10$^6$ cells/ml in Dulbecco's modified eagles medium, containing 10% fetal calf serum and 2 mM Glutamine.

The cells were stimulated with 2 µg/ml phytohemoagglutinin in the presence of test compound or blank vehicle for 72 h. 4 h prior to the end of the incubation period, 5-bromo-2'-desoxyuridine (BrdU) was added to label the proliferating cells. After the incubation, the cells were separated by centrifugation and the culture supernatant removed. Incorporated BrdU was quantified with the help of an enzyme-linked immunosorbent assay.

For the determination of the $IC_{50}$ values (concentration of inhibitor required for 50% inhibition) at least four different inhibitor concentrations were applied. Each data point was recorded in triplicates. Curves were fitted with the a suitable program.

Influence of Compounds According to the Invention on Proliferation of T-Cells

Compounds according to Examples 1-24 resulted in an inhibition of more than 50% compared to control experiments.

The average $EC_{50}$ of the compounds were between 3 and 40 µM.

Thus, the compounds of formula I are suitable for treating inflammatory diseases or diseases associated with Tcells.

Inhibition of NF-κB-Induced Inflammation:

For the determination of anti-inflammatory activity of the compounds the PRINCESS® NINA Instant Assay from Cell Culture Service GmBH was used. This assay is based on recombinant A549-NF-κB-SEAP reporter cells preceded in 96-well flat bottom plates. As the transfected reportergen for SEAP (secreted embryonic alkaline phosphatase) is under transcriptional control of a NF-κB-responsive element, the expression of this reporter is activated upon stimulation with TNF-α. SEAP secretion into the culture supernatant can be detected by the chemiluminescent substrate CSPD®. Test compounds that inhibit the NF-κB activation show reduced SEAP activity and reduced luminescent readout.

Following 18 h of reactivation at 37° C., 5% $CO_2$ and 90% relative humidity, the cells were incubated with 0.01 up to 100 µM of test compound for 4.5 h before stimulation with 2 ng/ml TNF-α. After stimulation with TNF-α for 22 h endogenous phosphatases were inactivated and CSPD® substrate was supplied for 40 min. SEAP activity then was quantified by measuring luminescence as relative light units (RLU) using a Tecan Ultra reader. Each data point was recorded in quadruplicates and EC50 values were calculated via fitting function and the Microsoft Excel Solver.

The invention claimed is:
1. A compound of the formula (I) and/or a salt thereof,

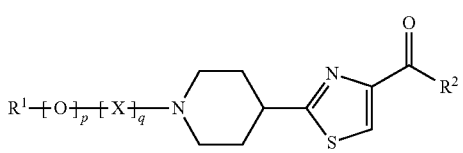 (I)

wherein
R$^1$ independently represents hydrogen, alkyl, cycloalkyl, hydroxyalkyl, haloalkyl, haloalkyloxy, aryl, substituted aryl, heteroaryl, substituted heteroaryl, arylalkyl or substituted arylalkyl;
R$^2$ independently represents —NR$^3$R$^4$,

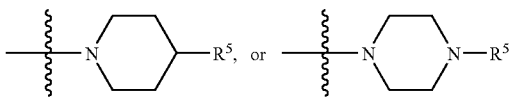

R$^3$ independently represents alkyl, cycloalkyl, alkoxy, alkylamine, —OH, —SH, alkylthio, hydroxyalkyl, haloalkyl, haloalkyloxy, aryl or heteroaryl,
R$^4$ independently represents alkyl, cycloalkyl, alkoxy, alkylamine, alkylthio, hydroxyalkyl, haloalkyl, haloalkyloxy, aryl or heteroaryl;
R$^5$ independently represents H, COR$^6$, CO$_2$R$^6$, SOR$^6$, SO$_2$R$^6$, SO$_3$R$^6$, alkyl, cycloalkyl, alkoxy, —NH$_2$, alkylamine, —NR$^7$COR$^6$, halogen, —OH, —SH, alkylthio, hydroxyalkyl, haloalkyl, haloalkyloxy, aryl or heteroaryl;
R$^6$ independently represents H, alkyl, cycloalkyl, —NH$_2$, alkylamine, aryl or heteroaryl;
R$^7$ independently represents H, alkyl, cycloalkyl, alkoxy, —OH, —SH, alkylthio, hydroxyalkyl, aryl, or heteroaryl;
p is 0, or 1;
q is 0, or 1;
X is CO or SO$_2$;
wherein an alkyl group, if not stated otherwise, denotes a linear or branched $C_1$-$C_6$-alkyl, preferably a linear or branched chain of one to five carbon atoms, a linear or branched $C_2$-$C_6$-alkenyl or a linear or branched $C_2$-$C_6$-alkinyl group, which can optionally be substituted by one or more substituents R';
wherein R' independently represents H, —CO$_2$R", —CONHR", —CR"O, —SO$_2$NR", —NR"-CO-haloalkyl, —NO$_2$, —NR"—SO$_2$-haloalkyl, —NR"—SO$_2$-alkyl, —SO$_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;
wherein R" independently represents H, haloalkyl, hydroxyalkyl, alkyl, cycloalkyl, aryl, heteroaryl or aminoalkyl;
wherein a cycloalkyl group denotes a non-aromatic ring system containing three to eight carbon atoms, wherein one or more of the carbon atoms in the ring can be substituted by a group E, E being O, S, SO, SO$_2$, N, or NR", R" being as defined above;

wherein an alkoxy group denotes an O-alkyl group, the alkyl group being as defined above;
the alkoxy group is preferably a methoxy, ethoxy, isopropoxy, t-butoxy or pentoxy group;
wherein an alkylthio group denotes an S-alkyl group, the alkyl group being as defined above;
wherein an haloalkyl group denotes an alkyl group which is substituted by one to five halogen atoms, the alkyl group being as defined above;
wherein a hydroxyalkyl group denotes an HO-alkyl group, the alkyl group being as defined above;
wherein a haloalkyloxy group denotes an alkoxy group which is substituted by one to five halogen atoms, the alkyl group being as defined above;
wherein a hydroxyalkylamino group denotes an (HO-alkyl)$_2$-N— group or HO-alkyl-NH-group, the alkyl group being as defined above;
wherein an alkylamino group denotes an HN-alkyl or N-dialkyl group, the alkyl group being as defined above;
wherein a halogen group is chlorine, bromine, fluorine or iodine;
wherein an aryl group denotes an aromatic group having five to fifteen carbon atoms, which can optionally be substituted by one or more substituents R', where R' is as defined above;
wherein a heteroaryl group denotes a 5- or 6-membered heterocyclic group which contains at least one heteroatom like O, N, S, wherein said heterocyclic group can be fused to another ring and can optionally be substituted by one or more substituents R', wherein R' is as defined above.
2. The compound according to claim 1 wherein p=0, q=1, and X=CO.
3. The compound according to claim 1 wherein p=0, q=1, and X=SO$_2$.
4. The compound according to claim 1 wherein p=1, q=1, and X=CO.
5. The compound according to claim 1 wherein p=1, q=1, and X=SO$_2$.
6. A compound of formula (III), or a salt, or a stereoisomer thereof,

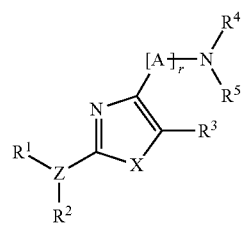 (III)

wherein
R$^1$ is —C(O)R$^7$, —C(O)CHR$^7$R$^8$, —C(O)NR$^7$R$^8$, —C(O)OR$^7$, —R$^7$C(O)R$^8$, —C(S)R$^7$, or R$^1$ and R$^2$ together with the Z to which they are attached form a 3 to 8 membered ring, wherein at least one ring atom is a heteroatom like O, N, S and the ring optionally has a substituent R$^9$;
R$^2$ is H, alkyl, cycloalkyl, heterocycloalkyl, haloalkyl, hydroxyalkyl, hydroxyalkylamino, alkylamino, heteroaryl, alkylaryl, aryl or R$^2$ is absent in the case Z forms a ring together with R$^1$;
R$^3$ is H, C(O)NR$^a$R$^b$ halogen, alkyl, haloalkyl, aryl or heteroaryl;

R⁴ is H, halogen, alkyl, —C(NR⁷)NR⁷R⁸, —(CH₂)ₚaryl, —(CH₂)ₚNR⁷R⁸, —C(O)NR⁷R⁸, —N═CR⁷R⁸, —NR⁷C(O)R⁸, cycloalkyl, heterocycloalkyl, haloalkyl, hydroxyalkyl, hydroxyalkylamino, alkylamino, heteroaryl, alkylaryl, or aryl;

R⁵ is H, halogen, alkyl, —C(NR⁷)NR⁷R⁸, —(CH₂)ₚaryl, —(CH₂)ₚNR⁷R⁸, —C(O)NR⁷R⁸, —N═CR⁷R⁸, —NR⁷C(O)R⁸, cycloalkyl, heterocycloalkyl, haloalkyl, hydroxyalkyl, hydroxyalkylamino, alkylamino, heteroaryl, alkylaryl, or aryl;

Rᵃ is H, halogen, alkyl, —C(NR⁷)NR⁷R⁸, —(CH₂)ₚaryl, —(CH₂)ₚNR⁷R⁸, —C(O)NR⁷R⁸, —N═CR⁷R⁸, —NR⁷C(O)R⁸, cycloalkyl, heterocycloalkyl, haloalkyl, hydroxyalkyl, hydroxyalkylamino, alkylamino, heteroaryl, alkylaryl, or aryl;

Rᵇ independently represents H, —CN, —OH, —SH, —CO₂R⁴', —C(O)R⁴', —SO₂NR⁴', —NR⁴R⁵', —C(O)NR⁷R⁸, —SO₂-alkyl, —SO₂R⁴', SO₃R⁴', —N═CR⁴R⁵', —NR⁴C(O)R⁴'', —NR⁴''—CO-haloalkyl, —NO₂, —NR⁴'—SO₂-haloalkyl, —NR⁴'—SO₂-alkyl, —NR⁴'—CO-alkyl, —NR⁴'(CH₂)ₚheterocycle, alkyl, cycloalkyl, alkylamino, alkoxy, alkylthio, —O(CH₂)ₚ[O(CH₂)ₚ]qOCH₃, —C(NR⁴'')NR⁴'benzimidazolyl, —C(NR⁴'')NR⁴'benzthiazolyl, —C(NR⁴'')NR⁴'benz-oxazolyl, hydroxyalkyl, hydroxycycloalkyl, hydroxyalkylamino, halogen, haloalkyl, haloalkyloxy, aryl, arylalkyl or a heterocycle;

R⁷, R⁷', R⁸ independently represent H, halogen, alkyl, cycloalkyl, heterocycloalkyl, haloalkyl, hydroxyalkyl, hydroxyalkylamino, alkylamino, —NHaryl, heteroaryl, alkylaryl, or aryl;

A is CO or SO₂;
X is NR²', O, S, or CR²';
Z is N or CR²'; if Z is CH then X is O or NR²'
R²' is H, alkyl, —C(O)NR², —C(O)Rᵇ, cycloalkyl, heterocycloalkyl, haloalkyl, hydroxyalkyl, hydroxyalkylamino, alkylamino, heteroaryl, alkylaryl, or aryl;
p is 1 to 6;
q is 1 to 6;
r is 0, or 1;

R⁹ independently represents H, —CN, —OH, —SH, —CO₂R⁴', —C(O)R⁴', —C(O)NR⁷R⁸, —SO₂NR⁴', —NR⁴'R⁵', —SO₂-alkyl, —SO₂R⁴', SO₃R⁴', —N═CR⁴R⁵', —NR⁴C(O)R⁴'', —NR⁴''—CO-haloalkyl, —NO₂, —NR⁴'—SO₂-haloalkyl, —NR⁴'—SO₂-alkyl, —NR⁴'—CO-alkyl, —NR⁴'(CH₂)ₚheterocycle, alkyl, cycloalkyl, alkylamino, alkoxy, alkylthio, —O(CH₂)ₚ[O(CH₂)ₚ]qOCH₃, —C(NR⁴'')NR⁴'benzimidazolyl, —C(NR⁴'')NR⁴'benzthiazolyl, —C(NR⁴'')NR⁴'benzoxazolyl hydroxyalkyl, hydroxycycloalkyl, hydroxyalkylamino, halogen, haloalkyl, haloalkyloxy, aryl, arylalkyl or a heterocycle;

R⁴', R⁴'', R⁵' independently represent H, halogen, alkyl, —C(NR⁷)NR⁷R⁸, —(CH₂)ₚaryl, —CH₂)ₚNR⁷R⁸, —C(O)NR⁷R⁸, —N═CR⁷R⁸, —NR⁷C(O)R⁸, cycloalkyl, heterocycloalkyl, haloalkyl, hydroxyalkyl, hydroxyalkylamino, alkylamino, heteroaryl, alkylaryl, or aryl wherein
an alkyl group, if not stated otherwise, denotes a linear or branched C₁-C₆-alkyl, a linear or branched C₂-C₆-alkenyl or a linear or branched C₂-C₆-alkynyl group, which can be substituted by one or more substituents R⁹; R⁹ being defined as above.
a heterocycle denotes a heterocycloalkyl group or a heteroaryl group;

a cycloalkyl group denotes a non-aromatic ring system containing three to eight carbon atoms, wherein one or more of the carbon atoms in the ring can be substituted by a group R⁹ being as defined above;

a heterocycloalkyl group denotes a non-aromatic ring system containing two to ten carbon atoms and at least one heteroatom like O, N, or S, wherein one or more of the carbon atoms in the ring can be substituted by R⁹ being as defined above;

an alkoxy group denotes an O-alkyl group, the alkyl group being as defined above;

an alkylthio group denotes an S-alkyl group, the alkyl group being as defined above;

an haloalkyl group denotes an alkyl group which is substituted by one to five halogen atoms, the alkyl group being as defined above;

a hydroxyalkyl group denotes an HO-alkyl group, the alkyl group being as defined above;

an haloalkyloxy group denotes an alkoxy group which is substituted by one to five halogen atoms, the alkyl group being as defined above;

a hydroxyalkylamino group denotes an (HO-alkyl)₂-N— group or HO-alkyl-NH— group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents R⁹, where R⁹ is as defined above;

a heteroaryl group denotes a 5- to 10-membered aromatic heterocyclic group which contains at least one heteroatom like O, N, S, wherein the heterocyclic group may be fused to another ring, and the heterocyclic group or the fused ring can both be substituted independently by one or more substituents R⁹, wherein R⁹ is as defined above;

a alkylaryl or arylalkyl group denotes an alkyl group as defined above, which is bound to an aryl fragment as defined above via a single bond, wherein the linkage to the central moiety occurs through the alkyl part or the aryl part.

7. A compound of formula (II), or a salt, or a stereoisomer thereof,

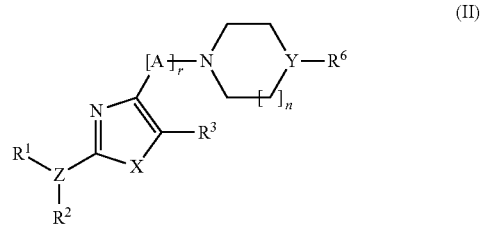

(II)

wherein
R¹ is —C(O)R⁷, —C(O)CHR⁷R⁸, —C(O)NR⁷R⁸, —C(O)OR⁷, —R⁷C(O)R⁸, —C(S)R⁷, or R¹ and R² together with the N-atom or the C-atom to which they are attached form a 3 to 8 membered ring, wherein at least one ring atom is a heteroatom like O, N, S and the ring optionally has a substituent R⁹;

R² is H, alkyl, cycloalkyl, heterocycloalkyl, haloalkyl, hydroxyalkyl, hydroxyalkylamino, alkylamino, heteroaryl, alkylaryl, aryl or R² is absent in the case Z forms a ring together with R¹;

$R^3$ is H, halogen, alkyl, haloalkyl, aryl or heteroaryl;

$R^6$ is H, halogen, —C(O)$R^7$, —C(O)CH$R^7R^8$, —C(O)N$R^7R^8$, —C(O)O$R^7$, —$R^7$C(O)$R^8$, —C(S)$R^7$, —C(N$R^7$)N$R^7R^8$, —(CH$_2$)$_p$aryl, —(CH$_2$)$_p$N$R^7R^8$, —C(O)N$R^7R^8$, —N=C$R^7R^8$, —N$R^7$C(O)$R^{7'}$, alkyl, cycloalkyl, heterocycloalkyl, haloalkyl, hydroxyalkyl, hydroxyalkylamino, alkylamino, heteroaryl, alkylaryl, or aryl;

$R^7$, $R^{7'}$, $R^8$ independently represent H, halogen, alkyl, cycloalkyl, heterocycloalkyl, haloalkyl, hydroxyalkyl, hydroxyalkylamino, alkylamino, —NHaryl, heteroaryl, alkylaryl, or aryl;

A is CO or SO$_2$;

X is N$R^{2'}$, O, S, or C$R^{2'}$;

Y is N, O, or C$R^{2'}$;

Z is N or C$R^{2'}$; if Z is CH then X is O or N$R^{2'}$ $R^{2'}$ is H, alkyl, —C(O)N$R^2$, —C(O)$R^b$, cycloalkyl, heterocycloalkyl, haloalkyl, hydroxyalkyl, hydroxyalkylamino, alkylamino, heteroaryl, alkylaryl, or aryl;

n is 0 to 2;

p is 1 to 6;

q is 1 to 6;

r is 0, or 1;

$R^9$ independently represents H, —CN, —OH, —SH, —CO$_2R^{4'}$, —C(O)$R^{4'}$, —C(O)N$R^7R^8$, —SO$_2$N$R^{4'}$, —N$R^{4'}R^{5'}$, —SO$_2$-alkyl, —SO$_2R^{4'}$, SO$_3R^{4'}$, —N=C$R^{4'}R^{5'}$, —N$R^{4'}$C(O)$R^{4''}$, —N$R^{4'}$—CO-haloalkyl, —NO$_2$, —N$R^{4'}$—SO$_2$-haloalkyl, —N$R^{4'}$—SO$_2$-alkyl, —N$R^{4'}$—CO-alkyl, —N$R^{4'}$(CH$_2$)$_p$heterocycle, alkyl, cycloalkyl, alkylamino, alkoxy, alkylthio, —O(CH$_2$)$_p$[O(CH$_2$)$_p$]$_q$OCH$_3$, —C(N$R^{4''}$)N$R^{4'}$benzimidazolyl, —C(N$R^{4''}$)N$R^{4'}$benzthiazolyl, —C(N$R^{4''}$)N$R^{4'}$benzoxazolyl hydroxyalkyl, hydroxycycloalkyl, hydroxyalkylamino, halogen, haloalkyl, haloalkyloxy, aryl, arylalkyl or a heterocycle;

$R^{4'}$, $R^{4''}$, $R^{5'}$ independently are H, halogen, alkyl, —C(N$R^7$)N$R^7R^8$, —(CH$_2$)$_p$aryl, —CH$_2$)$_p$N$R^7R^8$, —C(O)N$R^7R^8$, —N=C$R^7R^8$, —N$R^7$C(O)$R^8$, cycloalkyl, heterocycloalkyl, haloalkyl, hydroxyalkyl, hydroxyalkylamino, alkylamino, heteroaryl, alkylaryl, or aryl;

wherein an alkyl group, if not stated otherwise, denotes a linear or branched C$_1$-C$_6$-alkyl, a linear or branched C$_2$-C$_6$-alkenyl or a linear or branched C$_2$-C$_6$-alkynyl group, which can be substituted by one or more substituents $R^9$; $R^9$ being defined as above.

a heterocycle denotes a heterocycloalkyl group or a heteroaryl group;

a cycloalkyl group denotes a non-aromatic ring system containing three to eight carbon atoms, wherein one or more of the carbon atoms in the ring can be substituted by a group $R^9$ being as defined above;

a heterocycloalkyl group denotes a non-aromatic ring system containing two to ten carbon atoms and at least one heteroatom like O, N, or S, wherein one or more of the carbon atoms in the ring can be substituted by $R^9$ being as defined above;

an alkoxy group denotes an O-alkyl group, the alkyl group being as defined above;

an alkylthio group denotes an S-alkyl group, the alkyl group being as defined above;

an haloalkyl group denotes an alkyl group which is substituted by one to five halogen atoms, the alkyl group being as defined above;

a hydroxyalkyl group denotes an HO-alkyl group, the alkyl group being as defined above;

an haloalkyloxy group denotes an alkoxy group which is substituted by one to five halogen atoms, the alkyl group being as defined above;

a hydroxyalkylamino group denotes an (HO-alkyl)$_2$-N-group or HO-alkyl-NH-group, the alkyl group being as defined above;

an alkylamino group denotes an HN-alkyl or N-dialkyl group, the alkyl group being as defined above;

a halogen group is fluorine, chlorine, bromine, or iodine;

an aryl group denotes an aromatic group having five to fifteen carbon atoms, which can be substituted by one or more substituents $R^9$, where $R^9$ is as defined above;

a heteroaryl group denotes a 5- to 10-membered aromatic heterocyclic group which contains at least one heteroatom like O, N, S, wherein the heterocyclic group may be fused to another ring and the heterocyclic group or the fused ring can both be substituted independently by one or more substituents $R^9$, wherein $R^9$ is as defined above;

a alkylaryl or arylalkyl group denotes an alkyl group as defined above, which is bound to an aryl fragment as defined above via a single bond, wherein the linkage to the central moiety occurs through the alkyl part or the aryl part.

8. The compound according to claim 6 wherein $R^2$ and $R^3$ is H; A is CO; r is 1, and X is O or S.

9. The compound according to claim 6 wherein $R^4$ and $R^3$ is H; A is CO; A is CO; r is 1, and X is O or S, Z forms together with $R^1$ a 6-membered ring and $R^2$ is absent; and if Z is N then X is O or S, or if Z is C$R^{2'}$, X is O.

10. The compound according to claim 6 wherein $R^2$ and $R^3$ is H; A is CO; A is CO; r is 1, and X is O or S, Z is N, le is CO$R^7$; wherein $R^7$ is an optionally substituted phenyl and $R^5$ is C(N$R^7$)N$^7R^8$ wherein $R^8$ is a heterocycloalkyl.

11. The compound according to claim 6 wherein Z forms together with $R^1$ a 6-membered ring and $R^2$ is absent; A is CO; r is 1, Z is N, $R^3$ is H; X is O or S, A is CO and $R^5$ is C(N$R^7$)N$R^7R^8$ wherein $R^8$ is a heterocycloalkyl.

12. The compound according to claim 6 wherein Z forms together with $R^1$ a 6-membered ring and $R^2$ is absent; A is CO; A is CO; r is 1, X is O or S, and if Z is N, X is O or S, if Z is CH, X is O.

13. The compound according to claim 7 wherein A is CO; X is O or S, A is CO; r is 1, $R^3$ is H and Y is N$R^{2'}$ wherein $R^{2'}$ is optionally substituted phenyl.

14. The compound according to claim 7 wherein A is CO; X is O or S, A is CO; r is 1, $R^3$ is H and Y is N$R^{2'}$ wherein $R^{2'}$ is 3-substituted trifluoromethylphenyl.

15. A medicament comprising a compound according to claim 1.

16. A composition containing a compound according to claim 1 and a pharmaceutically acceptable carrier or diluent.

\* \* \* \* \*